(12) United States Patent
Jiang et al.

(10) Patent No.: US 7,671,045 B2
(45) Date of Patent: Mar. 2, 2010

(54) 17-PHOSPHOROUS STEROID DERIVATIVES USEFUL AS PROGESTERONE RECEPTOR MODULATORS

(75) Inventors: Weiqin Jiang, Cranbury, NJ (US); Zhihua Sui, Exton, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 392 days.

(21) Appl. No.: 11/675,652

(22) Filed: Feb. 16, 2007

(65) Prior Publication Data

US 2007/0207982 A1 Sep. 6, 2007

Related U.S. Application Data

(60) Provisional application No. 60/775,043, filed on Feb. 17, 2006.

(51) Int. Cl.
*A61K 31/56* (2006.01)
*A61K 31/58* (2006.01)
*C07J 43/00* (2006.01)
*C07J 51/00* (2006.01)

(52) U.S. Cl. .................. 514/176; 514/178; 514/866; 540/108; 552/506

(58) Field of Classification Search .............. 514/176, 514/178; 540/108; 552/506
See application file for complete search history.

(56) References Cited

U.S. PATENT DOCUMENTS 4,634,696 A    1/1987    Teutsch et al.

FOREIGN PATENT DOCUMENTS

EP    582338 B1    10/1999

OTHER PUBLICATIONS

Cook, C.E. et al.: Reversal of activity profile in analogs of the antiprogestin RU 486: effect of a 16α-substituent on progestational (agonist) activity. Life Sciences (1993) 52: 155-162.
Jiang, W. et al.: Discovery of novel phosphorous-containing steroids as selective glucocorticoid receptor antagonist. Bioorganic & Med. Chem Letters (2007) 17: 1471-1474.
Lundeen, S.G. et al.: "Rat uterine complement C3 expression as a model for progesterone receptor modulators: characterization of the new progestin trimegestone"; J. of Steroid Biochem & Molec Biology (2001) 78: 137-143.
Philibert, D. et al. "New Analogs of Mifepristone with More Dissociated Antiprogesterone Activities". Journal of Steroid Biochemistry (1989) 34(1-6): 413-417, XP002446928.
Wagner, B.L. et al.: 16α-substituted analogs of the antiprogestin RU486 induce a unique conformation in the human progesterone receptor resulting in mixed agonist activity; Proc. Natl. Acad. Sci. (1996) 93: 8739-8744.

*Primary Examiner*—Barbara P Badio

(57) ABSTRACT

The present invention is directed to novel 17-phosphorous steroid derivatives, pharmaceutical compositions containing them and their use in the treatment of disorders and conditions modulated by a progesterone or glucocorticoid receptor.

13 Claims, No Drawings

17-PHOSPHOROUS STEROID DERIVATIVES USEFUL AS PROGESTERONE RECEPTOR MODULATORS

CROSS REFERENCE TO RELATED APPLICATIONS

This application claims the benefit of U.S. Provisional Application 60/775,043, filed on Feb. 17, 2006, which is incorporated by reference herein in its entirety.

FIELD OF THE INVENTION

The present invention is directed to 17-phosphorous steroid derivatives, pharmaceutical compositions containing them and their use in the treatment of disorders and conditions modulated by a progesterone or glucocorticoid receptor. More particularly, the compounds of the present invention are useful in the treatment of disorders including, but not limited to, secondary amenorrhea; dysfunctional bleeding; uterine leiomyomata; endometriosis; polycystic ovary syndrome; carcinomas and adenocarcinomas of the endometrium, ovary, breast, colon and/or prostate, Type II diabetes mellitus, impaired oral glucose tolerance, elevated blood glucose levels and Syndrome X. The compounds of the present invention are further useful as contraceptives and for the minimization of side effects of cyclic menstrual bleeding (e.g. for the treatment of premenstrual syndrome) and for contraception.

BACKGROUND OF THE INVENTION

Intracellular receptors are a class of structurally related proteins involved in the regulation of gene proteins. Steroid receptors are a subset of these receptors, including the progesterone receptors (PR), androgen receptors (AR), estrogen receptors (ER), glucocorticoid receptors (GR) and mineralocorticoid receptors (MR). Regulation of a gene by such factors requires the intracellular receptor and a corresponding ligand which has the ability to selectively bind to the receptor in a way that affects gene transcription.

Progesterone receptor modulators (progestagens) are known to play an important role in mammalian development and homeostasis. Progesterone is known to be required for mammary gland development, ovulation and the maintenance of pregnancy. Currently, steroidal progestin agonists and antagonists are clinically approved for contraception, hormone replacement therapy (HRT) and therapeutic abortion. Moreover, there is good preclinical and clinical evidence for the value of progestin antagonists in treating endometriosis, uterine leiomyomata (fibroids), dysfunctional uterine bleeding and breast cancer.

The current steroidal progestagens have been proven to be quite safe and are well tolerated. Sometimes, however, side effects (e.g. breast tenderness, headaches, depression and weight gain) have been reported that are attributed to these steroidal progestagens, either alone or in combination with estrogenic compounds.

Steroidal ligands for one receptor often show cross-reactivity with other steroidal receptors. As an example, many progestagens also bind to glucocorticoid receptor. Non-steroidal progestagens have no molecular similarity with steroids and therefore one might also expect differences in physicochemical properies, pharmacokinetic (PK) parameters, tissue distribution (e.g. CNS versus peripheral) and, more importantly, non-steroidal progestagens may show no/less cross-reactivity to other steroid receptors. Therefore, non-steroidal progestagens will likely emerge as major players in reproductive pharmacology in the foreseeable future.

It was known that progesterone receptor existed as two isoforms, full-length progesterone receptor isoform (PR-B) and its shorter counterpart (PR-A). Recently, extensive studies have been implemented on the progesterone receptor knockout mouse (PRKO, lacking both the A- and B-forms of the receptors), the mouse knockoutting specifically for the PR-A isoform (PRAKO) and the PR-B isoform (PRBKO). Different phenotypes were discovered for PRKO, PRAKO and PRBKO in physiology studies in terms of fertility, ovulation uterine receptivity, uterine proliferation, proliferation of mammary gland, sexual receptivity in female mice, sexual activity in male mice and infanticide tendencies in male mice. These findings provided insights for synthetic chemists to construct not only selective progesterone receptor modulator (SPRM), but also PR-A or PR-B selective progesterone receptor modulator.

Progesterone plays a major role in reproductive health and functioning. Its effects on, for example, the uterus, breast, cervix and hypothalamic-pituitary unit are well established. The actions of progesterone as well as progesterone antagonists are mediated by the progesterone receptor (PR). In the target cell, progesterone produces a dramatic change in confirmation of the PR that is associated with transforming the PR from a non-DNA binding form to one that will bind to DNA. This transformation is accompanied by a loss of associated heat shock proteins and dimerization. The activated PR dimmer then binds to specific DNA sequences within the promotor region of progesterone responsive genes. The agonist-bound PR is believed to activate transcription by associating with coactivators, which act as bridging factors between the receptor and the general transcription machinery. This is followed by increases in the rate of transcription producing agonist effects at the cellular and tissue levels. These progesterone receptor ligands exhibit a spectrum of activity ranging from pure antagonists to mixed agonists/antagonists.

In 1982, the discovery of compounds that bind to the progesterone receptor, antagonize the effects of progesterone receptor and antagonize the effects of progesterone was announced. Although compounds such as estrogens and certain enzyme inhibitors can prevent the physiological effects of endogenous progesterone, the term "antiprogestin" is confined to those compounds that bind to the progestin receptor. A report from the Institute of Medicine (Donaldson, Molly S.; Dorflinger, L.; Brown, Sarah S.; Benet, Leslie Z., Editors, *Clinical Applications of Mifepristone (RU 486) and Other antiprogestins*, Committee on antiprogestins: Assessing the science, Institute of medicine, National Academy Press, 1993) summarized a number of medical conditions related to the effect of antiprogestins. In view of the pivotal role that progesterone plays in reproduction, it is not surprising that antiprogestins could play a part in fertility control, including contraception, menses induction and medical termination of pregnancy, but there are many other potential uses that have been supported by small clinical or preclinical studies, such as labor and delivery; treatment of uterine leiomyomas (fibroids), treatment of endometriosis; HRT; breast cancers; male contraception, etc.

The effects and uses of progesterone agonists have been well established. In addition, it has been recently shown that certain compounds structurally related to the known antiprogestins have agonist activity in certain biological systems (e.g., the classical progestin effects I the estrogen-primed immature rabbit uterus; cf. C. E. Cook et al., Life Sciences, 52, 155-162 (1993)). Such compounds are partial agonists in human cell-derived receptor systems, where they bind to a site distinct from both the progestin and antiprogestin sites (Wagner et al., Proc. Natl. Acad. Sci., 93, 8739-8744 (1996)). Thus the general class of antiprogestins can have subclasses, which may vary in their clinical profiles.

Compounds which mimic some of the effects of progesterone (agonists), antagonize these effects (antagonists, antiprogestins) or exhibit mixed effects (partial agonists or mixed agonist/antagonist), known as progesterone receptor modulators (PRMs) can be useful in treating a variety of disease states and conditions. PR agonists have been used in female contraceptives and in postmenopausal hormone therapy. Recent studies in women and non-human primates show that PR antagonists may also have potential as contraceptive agents and for the treatment of various gynecological and obstetric diseases, including fibroids, endometriosis and, possibly, hormone-dependent cancers. Clinically available PR agonists and antagonists are steroidal compounds and often cause various side effects due to their functional interaction with other steroid receptors. Recently, numerous receptor-selective non-steroidal PR agonists and antagonists have emerged. Non-steroidal PR antagonists, being structurally distinct from the steroid class, may have greater potential for selectivity against other steroid receptors.

SUMMARY OF THE INVENTION

The present invention is directed to compounds of formula (I)

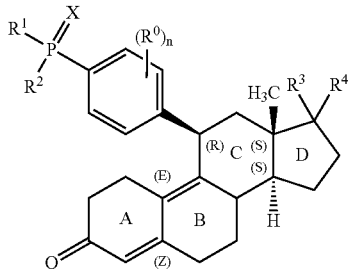

wherein n is an integer from 0 to 3;

$R^0$ is selected from the group consisting of hydroxy, halogen, $C_{1-3}$alkyl, $C_{1-3}$alkoxy, cyano, nitro, amino, ($C_{1-4}$alkylamino) and di($C_{1-4}$alkyl)amino;

X is selected from the group consisting of O and S;

$R^1$ and $R^2$ are each independently selected from the group consisting of hydroxy, $C_{1-4}$alkyl, —C(—O—$C_{1-4}$alkyl)$_2$, $C_{1-4}$alkoxy, halogenated $C_{1-4}$alkyl, halogenated $C_{1-4}$alkoxy, phenyl, —O-phenyl, —O-aralkyl and $NR^5R^6$;

wherein the phenyl, whether alone or as part of a substituent group, is optionally substituted with one or more substituents independently selected from hydroxy, carboxy, halogen, $C_{1-3}$alkyl, $C_{1-3}$alkoxy, cyano, nitro, amino, ($C_{1-4}$alkylamino) and di($C_{1-4}$alkyl)amino;

wherein $R^5$ and $R^6$ are each independently selected from the group consisting of hydrogen and $C_{1-4}$alkyl; alternatively, $R^5$ and $R^6$ are taken together with the nitrogen atom to which they are bound to form a 5- to 7-membered saturated or partially unsaturated nitrogen containing heterocyclyl ring; wherein the nitrogen containing heterocyclyl ring is optionally substituted with one or more substituents independently selected from hydroxy, carboxy, $C_{1-4}$alkyl, $C_{1-4}$alkoxy, nitro, cyano, amino, ($C_{1-4}$alkylamino) and di($C_{1-4}$alkyl)amino;

alternatively, $R^1$ and $R^2$ are taken together with the phosphorous atom to which they are bound to form a 5- to 7-membered saturated phosphorous containing heterocyclyl ring; wherein the phosphorous containing heterocyclyl ring is optionally substituted with one or more substituents independently selected from hydroxy, carboxy, $C_{1-4}$alkyl, $C_{1-4}$alkoxy, nitro, cyano, amino, ($C_{1-4}$alkylamino) and di($C_{1-4}$alkyl)amino;

$R^3$ is selected from the group consisting of —OH and —O—C(O)—$C_{1-4}$alkyl, —O—$C_{1-4}$alkyl and —O-benzyl;

$R^4$ is selected from the group consisting of hydrogen, $C_{1-4}$alkyl, $C_{2-4}$alkenyl, $C_{2-4}$alkynyl, —$C_{1-4}$alkyl-CN, halogenated $C_{1-4}$alkyl, —$C_{1-4}$alkyl-phenyl, —$C_{2-4}$alkenyl-phenyl and —$C_{2-4}$alkynyl-phenyl;

alternatively, $R^3$ and $R^4$ are taken together with the carbon atom to which they are bound to form C(=O) or a 5- to 7-membered oxygen containing, saturated or partially unsaturated ring structure; wherein the oxygen containing ring structure is further optionally substituted with one or more substituents independently selected from the group consisting of hydroxy, carboxy, $C_{1-4}$alkyl, $C_{1-4}$alkoxy, =$CH_2$, nitro, cyano, amino, ($C_{1-4}$alkylamino) and di($C_{1-4}$alkyl)amino;

and pharmaceutically acceptable salts, ester and prodrugs thereof.

The present invention is further directed to compounds of formula (II)

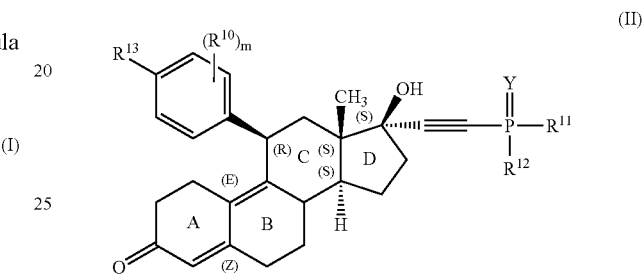

wherein m is an integer from 0 to 3;

$R^{10}$ is selected from the group consisting of hydroxy, halogen, $C_{1-3}$alkyl, $C_{1-3}$alkoxy, cyano, nitro, amino, ($C_{1-4}$alkylamino) and di($C_{1-4}$alkyl)amino;

Y is selected from the group consisting of O and S;

$R^{11}$ and $R^{12}$ are each independently selected from the group consisting of hydroxy, $C_{1-4}$alkyl, —C(—O—$C_{1-4}$alkyl)$_2$, $C_{1-4}$alkoxy, halogenated $C_{1-4}$alkyl, halogenated $C_{1-4}$alkoxy, phenyl, —O-phenyl, —O-aralkyl, 2-isoxazolidin-3-one and $NR^{15}R^{16}$;

wherein the phenyl, whether alone or as part of a substituent group, is optionally substituted with one or more substituents independently selected from hydroxy, carboxy, halogen, $C_{1-3}$alkyl, $C_{1-3}$alkoxy, cyano, nitro, amino, ($C_{1-4}$alkylamino) and di($C_{1-4}$alkyl)amino;

wherein $R^{15}$ and $R^{16}$ are each independently selected from the group consisting of hydrogen and $C_{1-4}$alkyl; alternatively, $R^{15}$ and $R^{16}$ are taken together with the nitrogen atom to which they are bound to form a 5- to 7-membered saturated or partially unsaturated nitrogen containing heterocyclyl ring; wherein the nitrogen containing heterocyclyl ring is optionally substituted with one or more substituents independently selected from hydroxy, carboxy, $C_{1-4}$alkyl, $C_{1-4}$alkoxy, nitro, cyano, amino, ($C_{1-4}$alkylamino) and di($C_{1-4}$alkyl)amino;

alternatively, $R^{11}$ and $R^{12}$ are taken together with the phosphorous atom to which they are bound to form a 5- to 7-membered saturated phosphorous containing heterocyclyl ring; wherein the phosphorous containing heterocyclyl ring is optionally substituted with one or more substituents independently selected from hydroxy, carboxy, $C_{1-4}$alkyl, $C_{1-4}$alkoxy, nitro, cyano, amino, ($C_{1-4}$alkylamino) and di($C_{1-4}$alkyl)amino;

$R^{13}$ is selected from the group consisting of —$NR^{17}R^{18}$; —O—$R^{19}$ and —S(O)$_{0-2}$—$R^{20}$;

wherein $R^{17}$ and $R^{18}$ are each independently selected from the group consisting of hydrogen and $C_{1-4}$alkyl; alternatively, $R^{17}$ and $R^{18}$ are taken together with the nitrogen atom to which they are bound to form a 5- to 7-membered saturated nitrogen containing heterocyclyl ring; wherein the nitrogen containing heterocyclyl ring is optionally substituted with one or more substituents independently selected from the group consisting of hydroxy, carboxy, $C_{1-4}$alkyl, $C_{1-4}$alkoxy, nitro, cyano, amino, ($C_{1-4}$alkylamino) and di($C_{1-4}$alkyl) amino;

$R^{19}$ is selected from the group consisting of $C_{1-4}$alkyl, —C(O)—$C_{1-4}$alkyl and —C(O)-phenyl;

$R^{20}$ is selected from the group consisting of hydrogen and $C_{1-4}$alkyl;

and pharmaceutically acceptable salts, ester and prodrugs thereof.

The present invention is further directed to the compound of formula (III)

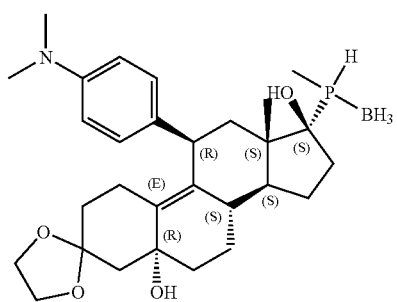

(III)

and pharmaceutically acceptable salts, ester and prodrugs thereof.

Illustrative of the invention is a pharmaceutical composition comprising a pharmaceutically acceptable carrier and the product prepared according to the process described herein. An illustration of the invention is a pharmaceutical composition made by mixing the product prepared according to the process described herein and a pharmaceutically acceptable carrier. Illustrating the invention is a process for making a pharmaceutical composition comprising mixing the product prepared according to the process described herein and a pharmaceutically acceptable carrier.

Exemplifying the invention are methods of treating a disorder mediated by at least one progesterone receptor comprising administering to a subject in need thereof a therapeutically effective amount of any of the compounds or pharmaceutical compositions described above.

In another embodiment, the compounds of the present invention are useful for the treatment of disorders mediated by at least one glucocorticoid receptor comprising administering to a subject in need thereof a therapeutically effective amount of any of the compounds or pharmaceutical compositions described above.

In another embodiment, the compounds of the present invention are useful for the treatment of a disorder selected from the group consisting of secondary amenorrhea; dysfunctional bleeding; uterine leiomyomata; endometriosis; polycystic ovary syndrome; carcinoma of the endometrium, carcinoma of the ovary, carcinoma of the breast, carcinoma of the colon, carcinoma of the prostate, adenocarcinomas of the ovary, adenocarcinomas of the breast, adenocarcinomas of the colon, adenocarcinomas of the prostate, side effects of cyclic menstrual bleeding or for contraception; comprising administering to a subject in need thereof a therapeutically effective amount of any of the compounds or pharmaceutical compositions described above.

In another embodiment, the compounds of the present invention are useful for the treatment of a disorder selected from the group consisting of Type II diabetes mellitus, impaired oral glucose tolerance, elevated blood glucose levels and Syndrome X; comprising administering to a subject in need thereof a therapeutically effective amount of any of the compounds or pharmaceutical compositions described above.

Another example of the invention is the use of any of the compounds described herein in the preparation of a medicament for treating of a progesterone or glucocorticoid receptor mediated disorder, (treating a disorder selected from (a) secondary amenorrhea; (b) dysfunctional bleeding; (c) uterine leiomyomata; (d) endometriosis; (e) polycystic ovary syndrome; (f) carcinoma of the endometrium, (g) carcinoma of the ovary, (h) carcinoma of the breast, (i) carcinoma of the colon, (j) carcinoma of the prostate, (k) adenocarcinomas of the ovary, (l) adenocarcinomas of the breast, (m) adenocarcinomas of the colon, (n) adenocarcinomas of the prostate, (o) side effects of cyclic menstrual bleeding, (p) Type II diabetes mellitus, (q) impaired oral glucose tolerance, (r) elevated blood glucose levels, (s) Syndrome X or (t) for contraception, in a subject in need thereof) in a subject in need thereof.

DETAILED DESCRIPTION OF THE INVENTION

The present invention is directed to compounds of formula (I) and formula (II)

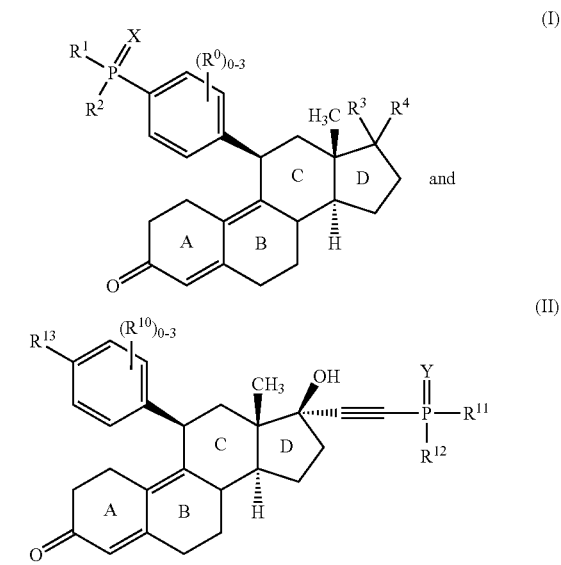

wherein X, n, $R^0$, $R^1$, $R^2$, $R^3$, $R^4$, Y, m, $R^{10}$, $R^{11}$, $R^{12}$ and $R^{13}$ are as herein defined and wherein the labels "A", "B", "C" and "D" represented the accepted designation of the four ring structures of the steroidal core. The compounds of formula (I) and formula (II) of the present invention are useful as progesterone receptor modulators and/or glucocorticoid receptor modulators, useful in the treatment of disorders including, but not limited to, secondary amenorrhea; dysfunctional bleeding; uterine leiomyomata; endometriosis; polycystic ovary syndrome; carcinoma of the endometrium, carcinoma of the ovary, carcinoma of the breast, carcinoma of the colon, carcinoma of the prostate, adenocarcinomas of the ovary, adenocarcinomas of the breast, adenocarcinomas of the colon, adenocarcinomas of the prostate, side effects of cyclic menstrual bleeding, Type II diabetes mellitus, impaired oral glucose tolerance, elevated blood glucose levels and Syndrome X or for contraception.

One skilled in the art will recognize that some of the variables (e.g. X, n, $R^0$, $R^1$, $R^2$, $R^3$, $R^4$, m, Y, $R^{10}$, $R^{11}$, $R^{12}$, $R^{13}$, etc.) appear in compounds of formula (I) and compounds of formula (II). One skilled in the art will further recognize that wherein a particular substituent is selected for a given variable for a compound of formula (I), said selection is not intended to limit the scope of said variable for compounds of formula (II). Similarly, the selection of a particular substituent for a given variable for a compound of formula (II), is not intended to limit the scope of said variable for compounds of formula (I).

In an embodiment of the present invention, X is O. In another embodiment of the present invention Y is O. In yet another embodiment of the present invention, Y is selected from the group consisting of O and S.

In an embodiment of the present invention, n is an integer from 0 to 2. In an embodiment of the present invention, n is an integer from 0 to 1. In another embodiment of the present invention, n is 0.

In an embodiment of the present invention, m is an integer from 0 to 2. In an embodiment of the present invention, m is an integer from 0 to 1. In another embodiment of the present invention, m is 0.

In an embodiment of the present invention, $R^0$ is selected from the group consisting of hydroxy, halogen and $C_{1-3}$alkyl, $C_{1-3}$alkoxy.

In an embodiment of the present invention, $R^{10}$ is selected from the group consisting of hydroxy, halogen and $C_{1-3}$alkyl, $C_{1-3}$alkoxy.

In an embodiment of the present invention $R^1$ and $R^2$ are the same. In another embodiment of the present invention $R^{11}$ and $R^{12}$ are the same.

In an embodiment of the present invention, $R^1$ and $R^2$ are each independently selected from the group consisting of hydroxy, $C_{1-4}$alkyl, —C(—O—$C_{1-4}$alkyl)$_2$, $C_{1-4}$alkoxy, fluorinated $C_{1-4}$alkyl, fluorinated $C_{1-4}$alkoxy, phenyl, —O-phenyl and —O-aralkyl; wherein the phenyl is optionally substituted with one to two substituents independently selected from hydroxy, carboxy, halogen, $C_{1-3}$alkyl and $C_{1-3}$alkoxy.

In another embodiment of the present invention, $R^1$ is selected from the group consisting of hydroxy, $C_{1-3}$alkyl, $C_{1-3}$alkoxy, fluorinated $C_{1-3}$alkoxy, phenyl, —O-aryl and O-benzyl; wherein the phenyl, whether alone or as part of a substituent group, is optionally substituted with a halogen.

In another embodiment of the present invention, $R^1$ is selected from the group consisting of hydroxy, methyl, methoxy, ethoxy, 2,2,2,-trifluoro-ethoxy-, phenyl, 4-chloro-phenyl, phenoxy and benzyloxy.

In another embodiment of the present invention, $R^1$ is selected from the group consisting of methyl, 2,2,2-trifluoro-ethyl, methoxy, ethoxy, phenyl, 1-(4-chlorophenyl) and phenoxy. In another embodiment of the present invention, $R^1$ is selected from the group consisting of methyl, ethoxy, phenyl and phenoxy.

In another embodiment of the present invention, $R^2$ is selected from the group consisting of $C_{1-3}$alkyl, $C_{1-3}$alkoxy, —C(—O—$C_{1-3}$alkyl)$_2$, fluorinated $C_{1-3}$alkoxy, phenyl, —O-aryl and O-benzyl; wherein the phenyl, whether alone or as part of a substituent group, is optionally substituted with a halogen.

In another embodiment of the present invention, $R^2$ is selected from the group consisting of methyl, methoxy, ethoxy, di(ethoxy)-methyl-, 2,2,2,-trifluoro-ethoxy-, phenyl, 4-chloro-phenyl, phenoxy and benzyloxy.

In another embodiment of the present invention, $R^2$ is selected from the group consisting of methyl, 2,2,2-trifluoro-ethyl, methoxy, ethoxy, phenyl, 1-(4-chlorophenyl) and phenoxy. In another embodiment of the present invention, $R^2$ is selected from the group consisting of methyl, ethoxy, phenyl and phenoxy.

In another embodiment of the present invention, $R^1$ and $R^2$ are taken together with the phosphorous atom to which they are bound to form a 5- to 6-membered saturated phosphorous containing heterocyclyl ring, wherein the phosphorous containing heterocyclyl ring is optionally substituted with one to two substituents independently selected from the group consisting of hydroxy, carboxy, $C_{1-4}$alkyl and $C_{1-4}$alkoxy.

In another embodiment of the present invention, $R^1$ and $R^2$ are taken together with the phosphorous atom to which they are bound to form a 6-membered saturated phosphorous containing heterocyclyl ring, wherein the phosphorous containing heterocyclyl ring is optionally substituted with one to two substituents independently selected from $C_{1-3}$alkyl. In another embodiment of the present invention, $R^1$ and $R^2$ are taken together with the phosphorous atom to which they are bound to form 2-(5,5-dimethyl-[1,3,2]dioxaphosphinane).

In an embodiment of the present invention, $R^3$ is selected from the group consisting of —OH, —O—C(O)—$C_{1-2}$alkyl, —O—$C_{1-2}$alkyl and —O-benzyl. In another embodiment of the present invention, $R^3$ is hydroxy. In another embodiment of the present invention, $R^3$ is selected from the group consisting of hydroxy, (S)-hydroxy and (R)-hydroxy. In another embodiment of the present invention, $R^3$ is selected from the group consisting of (R)-hydroxy and (S)-hydroxy.

In an embodiment of the present invention, $R^4$ is selected from the group consisting of $C_{1-4}$alkyl, $C_{2-4}$alkenyl, $C_{2-4}$alkynyl, —$C_{1-4}$alkyl-CN, fluorinated $C_{1-4}$alkyl and —$C_{2-4}$alkynyl-phenyl.

In another embodiment of the present invention, $R^4$ is selected from the group consisting of —$C_{1-3}$alkyl-CN, fluorinated $C_{1-3}$alkyl, $C_{2-4}$alkenyl, $C_{2-4}$alkynyl and —$C_{2-4}$alkynyl-phenyl.

In another embodiment of the present invention, $R^4$ is selected from the group consisting of —$CH_2$—CN, —$CF_2$—$CF_3$, —CC—$CH_3$, —$CH_2$—CH=$CH_2$, (R) —$CH_2$—CH=$CH_2$, —CH(=$CH_2$)—$CH_3$, —$CH_2$—CH=CH—$CH_2$ and —CC-phenyl.

In another embodiment of the present invention, $R^4$ is selected from the group consisting of —$CF_2$—$CF_3$, —CH(=$CH_2$)—$CH_3$, —$CH_2$—CH=$CH_2$ and —CC-phenyl. In another embodiment of the present invention, $R^4$ is selected from the group consisting of —CH(=$CH_2$)—$CH_3$, —$CH_2$—CH=$CH_2$, —CC—$CH_3$ and —CC-phenyl.

In an embodiment of the present invention, $R^3$ and $R^4$ are taken together with the carbon atom to which they are bound to form C(=O), a 5- to 6-membered oxygen containing, saturated or partially unsaturated ring structure; wherein the oxygen containing ring structure is further optionally substituted with one to two substituents independently selected from the group consisting of hydroxy, carboxy, $C_{1-4}$alkyl, $C_{1-4}$alkoxy and =$CH_2$.

In another embodiment of the present invention, $R^3$ and $R^4$ are taken together with the carbon atom to which they are bound to form C(O) or a membered saturated oxygen containing ring structure, wherein the oxygen containing ring structure is optionally substituted with =$CH_2$.

In another embodiment of the present invention, $R^3$ and $R^4$ are taken together with the carbon atom to which they are bound to form C(O) or 2-(3-methylene-tetrahydro-furanyl).

In an embodiment of the present invention, $R^{11}$ and $R^{12}$ are each independently selected from the group consisting of $C_{1-4}$alkyl, $C_{1-4}$alkoxy, fluorinated $C_{1-4}$alkyl, fluorinated $C_{1-4}$alkoxy, phenyl, 2-isoxazolidin-3-one and $NR^{15}R^{16}$; wherein $R^{15}$ and $R^{16}$ are each independently selected from $C_{1-3}$alkyl; wherein the phenyl, whether alone or as part of a substituent group, is optionally substituted with one to two substituents independently selected from hydroxy, carboxy, halogen, $C_{1-3}$alkyl and $C_{1-3}$alkoxy.

In an embodiment of the present invention, $R^{15}$ and $R^{16}$ are each independently selected from the group consisting of hydrogen and $C_{1-4}$alkyl; alternatively, $R^{15}$ and $R^{16}$ are taken together with the nitrogen atom to which they are bound to form a 5- to 6-membered saturated nitrogen containing heterocyclyl ring; wherein the nitrogen containing heterocyclyl ring is optionally substituted with one to two substituents independently selected from hydroxy, $C_{1-4}$alkyl and $C_{1-4}$alkoxy.

In another embodiment of the present invention, $R^{11}$ is selected from the group consisting of $C_{1-3}$alkyl, $C_{1-3}$alkoxy, phenyl, 2-isoxazolidin-3-one and $NR^{15}R^{16}$; wherein $R^{15}$ and $R^{16}$ are each independently selected from $C_{1-3}$alkyl.

In another embodiment of the present invention, $R^{11}$ is selected from the group consisting of methyl, methoxy, ethoxy, phenyl, 2-isooxazolidin-3-one and dimethylamino.

In another embodiment of the present invention, $R^{11}$ is selected from the group consisting of methyl, methoxy, ethoxy, phenyl and 2-isooxazolidin-3-one. In another embodiment of the present invention, $R^{11}$ is selected from the group consisting of methyl, methoxy, ethoxy and phenyl.

In another embodiment of the present invention, $R^{12}$ is selected from the group consisting of $C_{1-3}$alkyl, $C_{1-3}$alkoxy, phenyl and $NR^{15}R^{16}$; wherein $R^{15}$ and $R^{16}$ are each independently selected from $C_{1-3}$alkyl.

In another embodiment of the present invention, $R^{12}$ is selected from the group consisting of methyl, methoxy, ethoxy, phenyl, 2-isooxazolidin-3-one and dimethylamino.

In another embodiment of the present invention, $R^{12}$ is selected from the group consisting of methyl, methoxy, ethoxy, phenyl and 2-isooxazolidin-3-one. In another embodiment of the present invention, $R^{12}$ is selected from the group consisting of methyl, methoxy, ethoxy and phenyl.

In an embodiment of the present invention, $R^{13}$ is selected from the group consisting of —$NR^{17}R^{18}$, —O—$R^{19}$ and —S—$R^{20}$. In another embodiment of the present invention, $R^{13}$ is selected from the group consisting of —$N(CH_3)_2$, —O—$CH_3$ and —S—$CH_3$. In another embodiment of the present invention, $R^{13}$ is selected from the group consisting of —$N(CH_3)_2$ and —S—$CH_3$. In another embodiment of the present invention, $R^{13}$ is selected from the group consisting of —$N(CH_3)_2$ and —O—$CH_3$.

In an embodiment of the present invention, $R^{17}$ and $R^{18}$ are each independently selected from the group consisting of hydrogen and $C_{1-4}$alkyl; alternatively, $R^{17}$ and $R^{18}$ are taken together with the nitrogen atom to which they are bound to form a 5- to 6-saturated membered nitrogen containing heterocyclyl ring; wherein the nitrogen containing heterocyclyl ring is optionally substituted with one to two substituents independently selected from the group consisting of hydroxy, $C_{1-4}$alkyl and $C_{1-4}$alkoxy. In another embodiment of the present invention, $R^{17}$ and $R^{18}$ are each independently selected from $C_{1-3}$alkyl.

In an embodiment of the present invention, $R^{19}$ is selected from the group consisting of $C_{1-4}$alkyl and —C(O)—$C_{1-3}$alkyl. In another embodiment of the present invention, $R^{19}$ is selected from $C_{1-3}$alkyl.

In an embodiment of the present invention, $R^{20}$ is selected from the group consisting of hydrogen and $C_{1-4}$alkyl. In another embodiment of the present invention, $R^{20}$ is selected from $C_{1-3}$alkyl.

Additional embodiments of the present invention, include those wherein the substituents selected for one or more of the variables defined herein (i.e. X, n, $R^0$, $R^1$, $R^2$, $R^3$, $R^4$, m, Y, $R^{10}$, $R^{11}$, $R^{12}$ and $R^{13}$) are independently selected to be any individual substituent or any subset of substituents selected from the complete list as defined herein.

In another embodiment of the present invention is any single compound or subset of compounds selected from the representative compounds listed in Tables 1-2 below.

Representative compounds of the present invention are as listed in Table 1 to 2, below. One skilled in the art will recognize that in the designation of substituent groups listed in the Tables below, (S)- and (R)- are designations of the stereo-configuration of the particular substituent group within the compound of formula (I) or compound of formula (II).

TABLE 1

Representative Compounds of Formula (I)

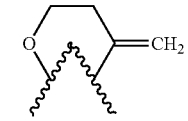

| ID No. | $R^1$ | $R^2$ | $R^3$ | $R^4$ |
|---|---|---|---|---|
| 1 | —O-ethyl | —O-ethyl | | =O |
| 2 | -methyl | -methyl | | =O |
| 3 | —O-ethyl | —O-ethyl | | 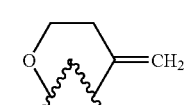 |
| 4 | -methyl | -methyl | | 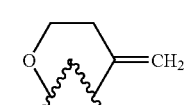 |

TABLE 1-continued

Representative Compounds of Formula (I)

| ID No. | $R^1$ | $R^2$ | $R^3$ | $R^4$ |
|---|---|---|---|---|
| 5 | -methyl | -methyl | —OH | —CC—$CH_3$ |
| 6 | -methyl | -methyl | —(R)—OH | —$CH_2$—CN |
| 7 | -methyl | -methyl | —(S)—OH | —$CF_2$—$CF_3$ |
| 8 | —O-ethyl | —O-ethyl | —(S)—OH | —$CF_2$—$CF_3$ |
| 9 | -methyl | -methyl | —(R)—OH | —$CH_2$—CH=$CH_2$ |
| 10 | -methyl | -methyl | —(R)—OH | —CH(=$CH_2$)—$CH_3$ |
| 11 | —O-ethyl | —O-ethyl | —(R)—OH | —CH(=$CH_2$)—$CH_3$ |
| 12 | —O-ethyl | —CH(O-ethyl)$_2$ | —(R)—OH | —(R)—$CH_2$—CH=$CH_2$ |
| 13 | —O-ethyl | —O-ethyl | —(R)—OH | —$CH_2$—CH=$CH_2$ |
| 14 | —OH | —O-ethyl | | =O |
| 15 | —O-methyl | —O-methyl | | =O |
| 16 | —O-methyl | —O-methyl | | (cyclic ether with =$CH_2$) |
| 17 | —OH | —O-methyl | | (cyclic ether with =$CH_2$) |
| 18 | —OH | —O-methyl | | =O |
| 19 | -methyl | —O-methyl | | (cyclic ether with =$CH_2$) |
| 20 | —OH | -methyl | | =O |
| 21 | -methyl | —O-ethyl | | =O |
| 22 | —OH | -methyl | | (cyclic ether with =$CH_2$) |
| 23 | (cyclic phosphonate with gem-dimethyl) | | —(R)—OH | —$CH_2$—CH=$CH_2$ |
| 24 | phenyl | phenyl | —(R)—OH | —$CH_2$—CH=$CH_2$ |
| 25 | —O-ethyl | —O-ethyl | —(S)—OH | —CC-phenyl |
| 26 | —O-ethyl | —O-ethyl | —(S)—OH | —CC—$CH_3$ |
| 27 | -phenyl | -phenyl | —(S)—OH | —CC—$CH_3$ |
| 28 | -phenyl | -phenyl | —(R)—OH | —$CH_2$—CH=CH—$CH_2$ |
| 29 | —O-ethyl | —O-ethyl | —(R)—OH | —$CH_2$—CH=CH—$CH_2$ |
| 30 | -phenyl | -phenyl | —(S)—OH | —CC-phenyl |
| 31 | —O-methyl | —O-methyl | —(S)—OH | —CO-phenyl |
| 32 | —O—$CH_2$—$CF_3$ | —O—$CH_2$—$CF_3$ | | =O |
| 33 | —O-phenyl | —O-phenyl | | =O |

TABLE 1-continued

Representative Compounds of Formula (I)

| ID No. | R¹ | R² | R³ | R⁴ |
|---|---|---|---|---|
| 34 | 1-(4-chloro-phenyl) | 1-(4-chloro-phenyl) | | =O |
| 35 | —O-benzyl | —O-benzyl | | =O |
| 36 | -phenyl | -phenyl | | (tetrahydropyran-4-ylidene-CH₂) |
| 37 | —O-phenyl | —O-phenyl | | (tetrahydropyran-4-ylidene-CH₂) |
| 38 | —O—CH₂—CF₃ | —O—CH₂—CF₃ | | (tetrahydropyran-4-ylidene-CH₂) |
| 39 | 1-(4-chloro-phenyl) | 1-(4-chloro-phenyl) | | (tetrahydropyran-4-ylidene-CH₂) |

TABLE 2

Representative Compounds of Formula (II)

| ID No. | Y | R¹¹ | R¹² | R¹³ |
|---|---|---|---|---|
| 101 | O | —O-ethyl | —O-ethyl | —N(CH₃)₂ |
| 102 | O | -methyl | -methyl | —N(CH₃)₂ |
| 103 | O | -phenyl | -phenyl | —N(CH₃)₂ |
| 104 | O | 2-isoxazolidin-3-one | 2-isoxazolidin-3-one | —N(CH₃)₂ |
| 105 | S | —O-methyl | —O-methyl | —N(CH₃)₂ |
| 106 | O | —N(CH₃)₂ | —N(CH₃)₂ | —N(CH₃)₂ |
| 107 | O | —O-ethyl | —O-ethyl | —S—CH₃ |
| 108 | O | —O-ethyl | —O-ethyl | —O—CH₃ |

As used herein, "halogen" shall mean chlorine, bromine, fluorine and iodine.

As used herein, the term "alkyl" whether used alone or as part of a substituent group, include straight and branched chains. For example, alkyl radicals include methyl, ethyl, propyl, isopropyl, butyl, isobutyl, sec-butyl, t-butyl, pentyl and the like. Unless otherwise noted, "$C_{1-4}$alkyl" shall mean a carbon chain composition of 1-4 carbon atoms.

As used herein, the term "alkenyl" whether used alone or as part of a substituent group, include straight and branched chains comprising at least one unsaturated double bond (preferably one to two, more preferably one unsaturated double bond). For example, alkenyl radicals include —CH=CH$_2$, 2-propenyl, 3-propenyl, 2-butenyl, 3-butenyl, and the like. Unless otherwise noted, "$C_{1-4}$alkenyl" shall mean an alkenyl carbon chain composition of 1-4 carbon atoms.

As used herein, the term "alkynyl" whether used alone or as part of a substituent group, include straight and branched chains. For example, alkenyl radicals include —C≡CH, 2-propynyl, 3-propynyl, 2-butynyl, 3-butynyl, and the like. Unless otherwise noted, "$C_{1-4}$alkynyl" shall mean an alkynyl carbon chain composition of 1-4 carbon atoms.

As used herein, unless otherwise noted, the term "halogenated $C_{1-4}$alkyl" shall mean any $C_{1-4}$alkyl group as defined above substituted with at least one halogen atom, preferably substituted with a least one fluoro atom. Suitable examples include but are not limited to —CF$_3$, —CH$_2$—CF$_3$, —CF$_2$—CF$_2$—CF$_2$—CF$_3$, and the like.

As used herein, unless otherwise noted, the term "fluorinated $C_{1-4}$alkyl" shall mean any $C_{1-4}$alkyl group as defined above substituted with at least one fluorine atom, preferably substituted with a least one fluoro atom. Suitable examples include but are not limited to —CF$_3$, —CH$_2$—CF$_3$, —CF$_2$—CF$_2$—CF$_2$—CF$_3$, and the like.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, unless otherwise noted, the term "halogenated $C_{1-4}$alkoxy" shall mean any $C_{1-4}$alkoxy group as defined above substituted with at least one halogen atom, preferably substituted with a least one fluoro atom. Suitable examples include but are not limited to —OCF$_3$, —OCH$_2$—CF$_3$, —OCF$_2$—CF$_2$—CF$_2$—CF$_3$, and the like.

As used herein, unless otherwise noted, the term "fluorinated $C_{1-4}$alkoxy" shall mean any $C_{1-4}$alkoxy group as defined above substituted with at least one fluorine atom, preferably substituted with a least one fluoro atom. Suitable examples include but are not limited to —OCF$_3$, —OCH$_2$—CF$_3$, —OCF$_2$—CF$_2$—CF$_2$—CF$_3$, and the like.

As used herein, unless otherwise noted, "aralkyl" shall mean any lower alkyl group substituted with an aryl group such as phenyl, naphthyl and the like. For example, benzyl, phenylethyl, phenylpropyl, naphthylmethyl, and the like, preferably benzyl.

As used herein, unless otherwise noted, the term "saturated or partially unsaturated nitrogen containing heterocyclyl ring" shall mean any ring structure of comprising the designated number of ring atoms, comprising at least one nitrogen atom, further comprising one to two additional heteroatoms (preferably one additional heteroatom) independently selected from N, O or S, (preferably N or O); and wherein the ring structure is saturated (i.e. contains no double bonds) or is partially unsaturated (i.e. contains at least one unsaturated double bond), but wherein the ring structure is not aromatic. Suitable examples include, but are not limited to, pyrrolidinyl, imidazolidinyl, imidazolinyl, pyrazolinyl, pyrazolidinyl, piperidinyl, piperazinyl, morpholinyl, thiomorpholinyl, 1,2,3,4-tetrahydro-pyridinyl, and the like.

As used herein, unless otherwise noted, the term "saturated phosphorous containing heterocyclyl ring" shall mean any ring structure of comprising the designated number of ring atom, comprising at least one nitrogen atom, further comprising one to three, preferably one to two additional heteroatom independently selected from N, O or S, (preferably N or O, more preferably O) and wherein the ring structure is saturated (i.e. contains no unsaturated, double bonds). Suitable examples include, but are not limited to, 2-[1,3,2]dioxaphosphinane, and the like, As used herein, unless otherwise noted, the term "saturated or partially unsaturated oxygen containing ring structure" shall mean any ring structure of comprising the designated number of ring atom, comprising at least one nitrogen atom, further comprising one or three, preferably one to two additional heteroatom independently selected from N, O or S, (preferably N or O); and wherein the ring structure is saturated (i.e. contains no double bonds) or is partially unsaturated (i.e. contains at least one unsaturated double bond), but wherein the ring structure is not aromatic. Suitable examples include, but are not limited to, tetrahydrofuryl, 1,4-dioxanyl, 4H-pyranyl, 2,3-dihydro-furyl, and the like.

As used herein, the notation "*" shall denote the presence of a stereogenic center.

When a particular group is "substituted" (e.g., phenyl, aryl, heterocycloalkyl, heteroaryl), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

As used herein, unless otherwise noted, the term "aprotic solvent" shall mean any solvent that does not yield a proton. Suitable examples include, but are not limited to DMF, dioxane, THF, acetonitrile, pyridine, dichloroethane, dichloromethane, MTBE, toluene, and the like.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, CH$_2$=CH—CH$_2$—, and the like; amides—groups of the formula —C(O)—R' wherein R' is for example methyl, phenyl, trifluoromethyl, and the like; N-sulfonyl derivatives—groups of the formula —SO$_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

Under standard nomenclature used throughout this disclosure, the terminal portion of the designated side chain is described first, followed by the adjacent functionality toward the point of attachment. Thus, for example, a "phenylC$_1$-C$_6$alkylaminocarbonylC$_1$-C$_6$alkyl" substituent refers to a group of the formula

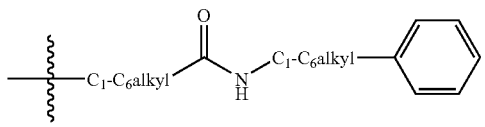

Abbreviations used in the specification, particularly the Schemes and Examples, are as follows:

| | |
|---|---|
| DCM = | Dichloromethanl |
| DIPEA or DIEA = | Diisopropylethylamine |
| DMF = | N,N-Dimethylformamide |
| DMSO = | Dimethylsulfoxide |
| dppb = | 1,4-Bis(diphenylphosphino)butane |
| dppp = | 1,3-Bis(diphenylphosphino)propane |
| EtOAc = | Ethyl acetate |
| FBS = | Fetal Bovine serum |
| Hex = | Hexanes |
| HPLC = | High Pressure Liquid Chromatography |
| KOtBu = | Potassium t-butoxide |
| LHMDS or LiHMDS = | Lithium bis(trumethylsilyl)amide |
| mCPBA = | 2-(4-Chloro-2-methylphenoxy)-Butyric acid |
| MeOH = | Methanol |
| MTBE = | Methyl t-Butyl Ether |
| NaOtBu = | Sodium t-Butoxide |
| n-BuLi = | n-Butyl Litiuhm |
| NMR = | Nuclear Magnetic Resonance |
| Pd$_2$(OAc)$_2$ = | Palladium(II)acetate |
| Ph = | Phenyl |
| PPh$_3$ = | Triphenyl phosphine |
| p-TSA = | para-Toluene Sulfonic Acid |
| RT or rt = | Room temperature |
| t-Bu of tBu = | Tert-butyl (—C(CH$_3$)$_3$) |
| TEA = | Triethylamine |
| THF = | Tetrahydrofuran |
| THPO = | Tetrahydro-2-H-pyranyl-oxy- |
| Tf = | Triflate (i.e. —O—SO$_2$—CF$_3$) |
| TLC = | Thin Layer Chromatography |

As sued herein, unless otherwise noted, the term "disorder mediated by at least one progesterone receptor" shall include any disorder whose symptoms and/or underlying cause may be mediated, treated or prevented by the agonism or antagonism of at least one progesterone receptor. Suitable examples include, butt are not limited secondary amenorrhea; dysfunctional bleeding; uterine leiomyomata; endometriosis; polycystic ovary syndrome; carcinoma of the endometrium, carcinoma of the ovary, carcinoma of the breast, carcinoma of the colon, carcinoma of the prostate, adenocarcinomas of the ovary, adenocarcinomas of the breast, adenocarcinomas of the colon, adenocarcinomas of the prostate, side effects of cyclic menstrual bleeding, and the like. Compounds of the present invention which modulate at least one progesterone receptor are further useful as contraceptive agents.

As used herein, unless otherwise noted, the term "disorder mediated by at least one glucocorticoid receptor" shall include any disorder whose symptoms and/or underlying cause may be mediated, treated or prevented by the agonism or antagonism of at least one progesterone receptor. Suitable examples include, butt are not limited Type II diabetes mellitus, impaired oral glucose tolerance, elevated glucose levels, Syndrome X, and the like.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Compounds of formula (I) wherein R$^3$ and R$^4$ are taken together with the atom to which they are bound to form an oxygen containing ring structure, more specifically 3-methylene-tetrahydro-furan, where the tetrahydrofuran is bound to the rest of the compound through the 2-position may be prepared according to the process outlined in Scheme 1.

Scheme 1

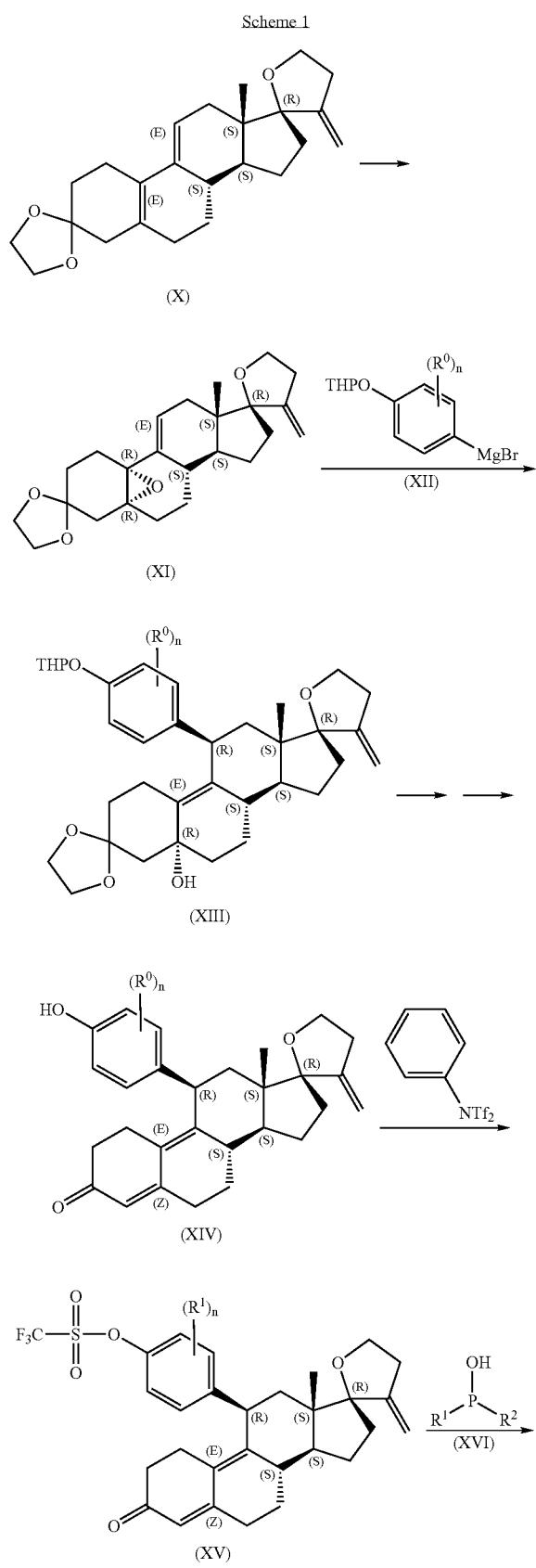

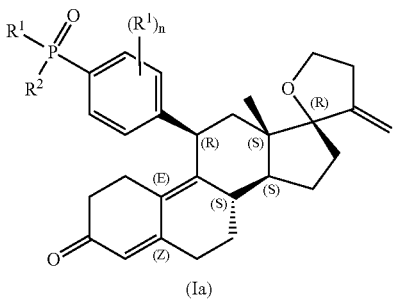

Accordingly, a suitably substituted compound of formula (X), a known compound or compound prepared by known methods, is reacted with a suitably selected oxidizing agent such as mCPBA, hydrogen peroxide, tBuOOH, and the like, in an organic solvent such as methylene chloride, dichloroethane, chlorobenzene, and the like, to yield the corresponding compound of formula (XI).

The compound of formula (XI) is reacted with a suitably substituted Grignard reagent, a compound of formula (XII), a known compound or compound prepared by known methods, in the presence of CuCl, in an organic solvent such as THF, 1,4-dioxane, diethyl ether, and the like, to yield the corresponding compound of formula (XIII).

The compound of formula (XIII) is de-protected under the catalytic amount of acid, such as oxalic acid, p-toluene sulfonic acid, acetic acid, trifluoroacetic acid and the like, in a mixture of an organic solvent such as acetone, 1,4-dioxane, THF, and the like and water, to yield the corresponding compound of formula (XIV).

The compound of formula (XIV) is reacted with N-phenyltrifluoromethanesulfonimide, a known compound, in the presence of a base such as NaH, KOtBu, LiHMDS, NaOtBu, and the like, in an organic solvent such as THF, 1,4-dioxane, diethyl ether, 1,2-dimethoxy-ethane, and the like, to yield the corresponding compound of formula (XV).

The compound of formula (XV) is reacted with a suitably substituted compound of formula (XVI), a known compound or compound prepared by known methods, in the presence of a phosphine ligand such as dppb, PPh$_3$, dppp, and the like, in the presence of a base such as TEA, DIPEA, pyridine, and the like, in an organic solvent such as DMSO, 1,4-dioxane, THF, DMF and the like, to yield the corresponding compound of formula (Ia).

One skilled in the art will recognize that compound of formula (I) wherein $R^3$ and $R^4$ are taken together with the atom to which they are bound to form an oxygen containing ring structure other than the one exemplified above may be similarly prepared according to the procedure described in Scheme 1 above, by selecting and substituting a suitably substituted steroidal derivative for the compound of formula (X) above.

Compounds of formula (I) wherein $R^3$ is —OH may be prepared according to the procedure outlined in Scheme 2 below.

Scheme 2

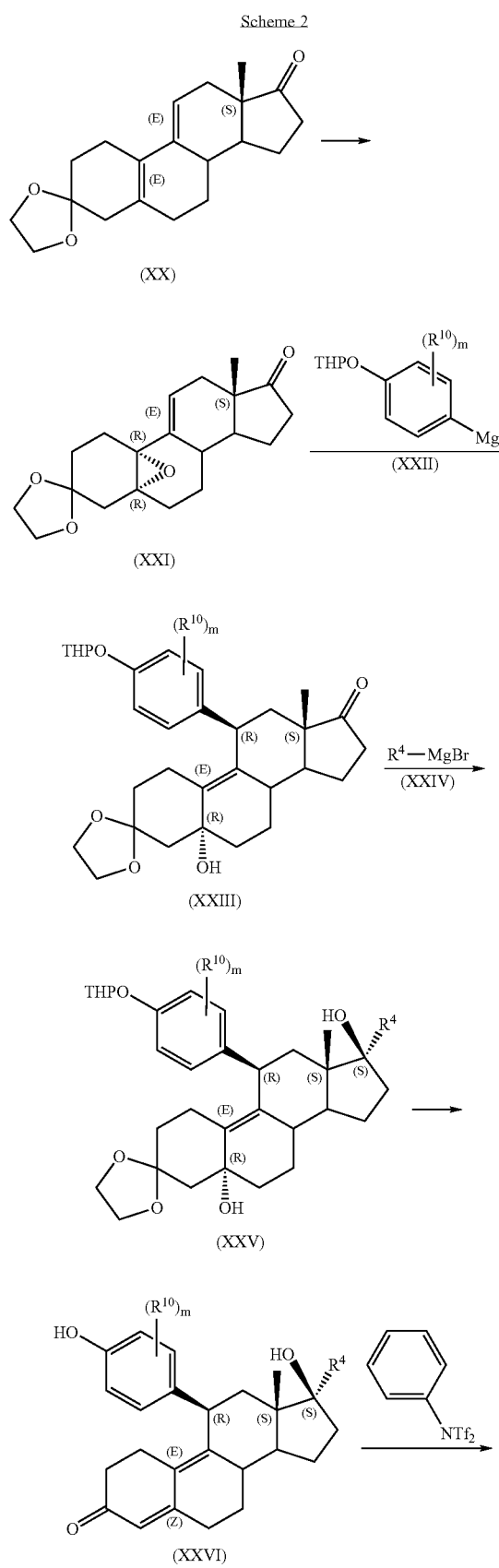

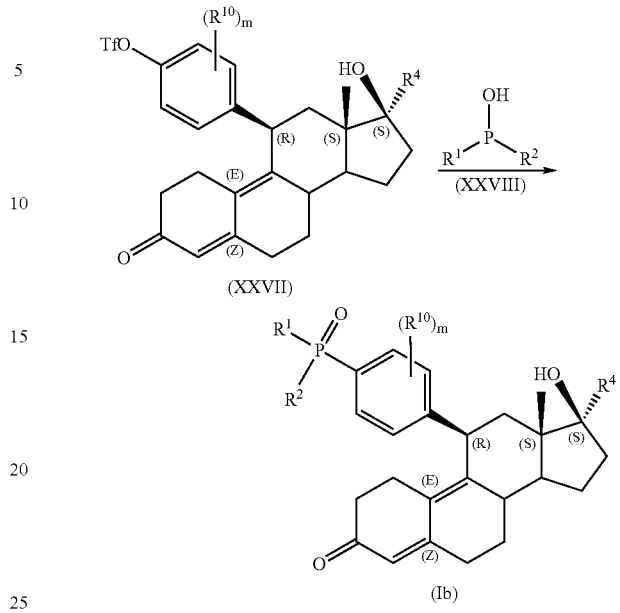

Accordingly, a suitably substituted compound of formula (XX), a known compound or compound prepared by known methods, is reacted with a suitably selected oxidizing agent such as mCPBA, hydrogen peroxide, tBuOOH, and the like, in an organic solvent such as dichloromethane, 1,2-dichloroethane, chlorobenzene, and the like, to yield the corresponding compound of formula (XXI).

The compound of formula (XXI) is reacted with a suitably substituted Grignard reagent, a compound of formula (XXII), a known compound or compound prepared by known methods, in the presence of CuCl, in an organic solvent such as THF, diethyl ether, 1,4-dioxane, and the like, to yield the corresponding compound of formula (XXIII).

The compound of formula (XXIII) is reacted with a suitably substituted compound of formula (XXIV), a suitably substituted Grignard reagent, a known compound or compound prepared by known methods, in an organic solvent such as THF, 1,4-dioxane, diethyl ether, and the like, to yield the corresponding compound of formula (XXV).

The compound of formula (XXV) is reacted with oxalic acid, in a mixture of an organic solvent such as acetone, THF, diethyl ether, and the like and water, to yield the corresponding compound of formula (XXIV).

The compound of formula (XXIV) is reacted with N-phenyltrifluoromethanesulfonimide, a known compound, in the presence of a base such as NaH, KotBu, NaOtBu, LiHMDS, and the like, in an organic solvent such as THF, DMF, DMSO, 1,4-dioxane, and the like, to yield the corresponding compound of formula (XXVII).

The compound of formula (XXVII) is reacted with a suitably substituted compound of formula (XVIII), a known compound or compound prepared by known methods, in the presence of a phosphine ligand such as dppb, PPh$_3$, dppp, and the like, in the presence of a base such as TEA, DIPEA, pyridine, and the like, in an organic solvent such as DMSO, DMF, THF, and the like, to yield the corresponding compound of formula (Ib).

One skilled in the art will recognize that compound of formula (I) wherein R$^3$ is other than —OH may be prepared accordingly by reacting the compound of formula (I) wherein $R^3$ is —OH according to known methods.

Compounds of formula (II) may be prepared according to the process outlined in Scheme 3 below.

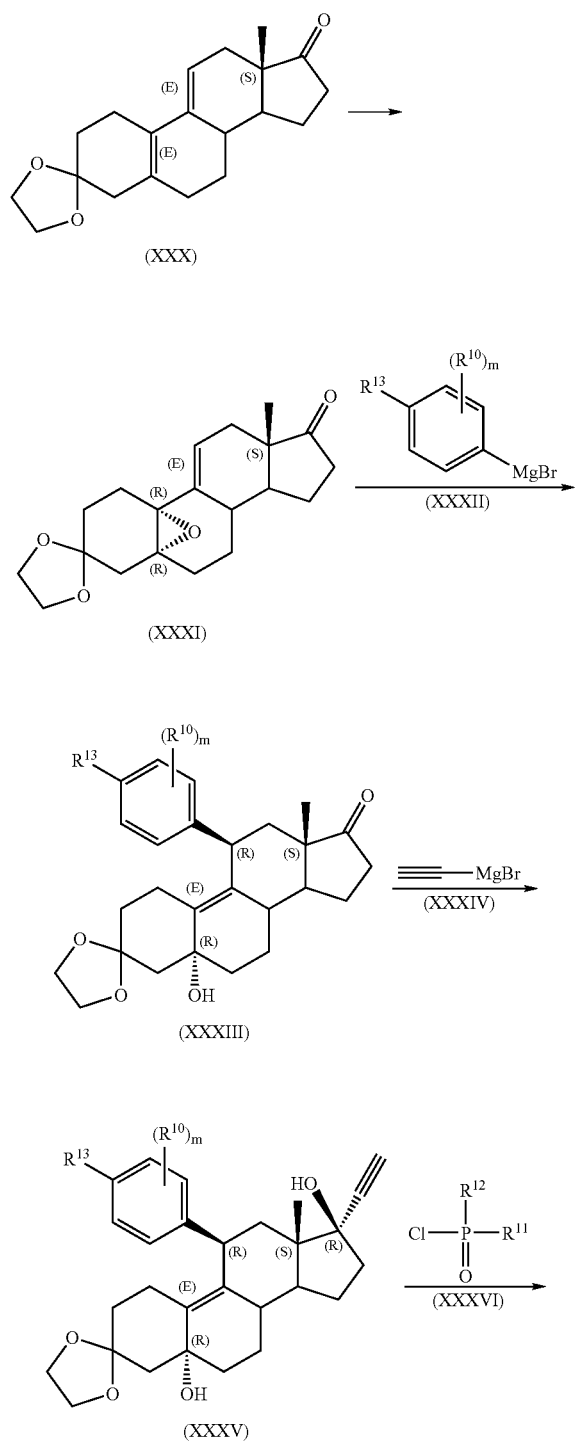

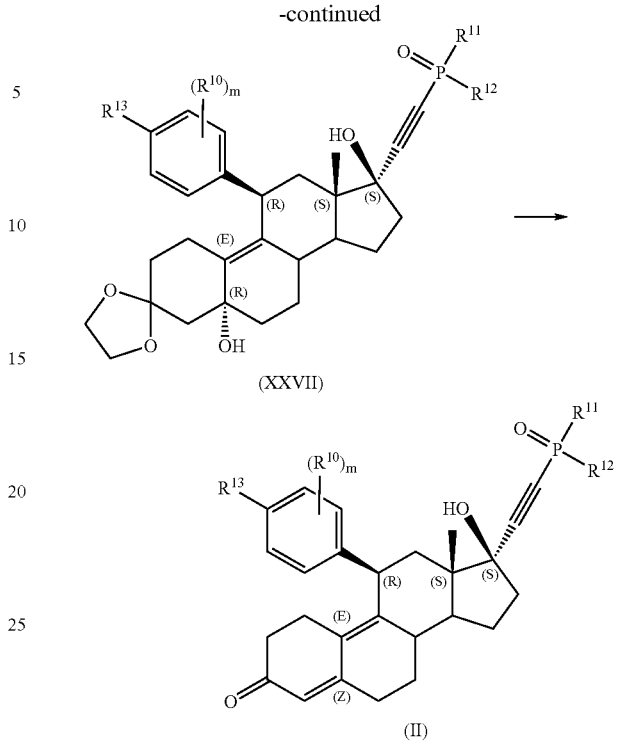

Accordingly, a suitably substituted compound of formula (XXX), a known compound or compound prepared by known methods is reacted with oxalic acid, in a mixture of an organic solvent such as acetone, THF, 1,4-dioxane, and the like and water, to yield the corresponding compound of formula (XXXI).

The compound of formula (XXXI) is reacted with a suitably substituted Grignard reagent, a compound of formula (XXXII), a known compound or compound prepared by known methods, in the presence of CuCl, in an organic solvent such as THF, 1,4-dioxane, diethyl ether, and the like, to yield the corresponding compound of formula (XXXIII).

The compound of formula (XXXIII) is reacted with a suitably substituted compound of formula (XXXIV), a suitably substituted Grignard reagent, a known compound or compound prepared by known methods, in an organic solvent such as THF, 1,4-dioxane, diethyl ether, and the like, to yield the corresponding compound of formula (XXXV).

The compound of formula (XXXV) is reacted with a suitably substituted compound of formula (XXXVI), a known compound or compound prepared by known methods, in the presence of a base such as LiHMDS, NaOtBu, KOtBu, NaH, and the like, in an organic solvent such as THF, 1,4-dioxane, DMF, DMSO, and the like, to yield the corresponding compound of formula (XXXVII).

The compound of formula (XXXVII) is de-protected under the catalytic amount of an acid such as p-TSA, oxalic acid, acetic acid, and the like, in an organic solvent such as acetone, THF, 1,4-dioxane, and the like, to yield the corresponding compound of formula (II).

One skilled in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following:

acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydrocy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lacetic acid, (±)-DL-lacetic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitric acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The present invention further comprises pharmaceutical compositions containing one or more compounds of formula (I) and/or one or more compounds of formula (II) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 50-100 mg and may be given at a dosage of from about 0.1-5.0 mg/kg/day, preferably from about 0.5-2.5 mg/kg/day. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The methods of treating of the present invention may also be carried out using a pharmaceutical composition comprising any of the compounds as defined herein and a pharmaceutically acceptable carrier. The pharmaceutical composition may contain between about 0.1 mg and 500 mg, preferably about 50 to 100 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in The Handbook of Pharmaceutical Excipients, published by the American Pharmaceutical Association and the Pharmaceutical Society of Great Britain.

Methods of formulating pharmaceutical compositions have been described in numerous publications such as Pharmaceutical Dosage Forms: Tablets, Second Edition, Revised and Expanded, Volumes 1-3, edited by Lieberman et al; Pharmaceutical Dosage Forms: Parenteral Medications, Volumes 1-2, edited by Avis et al; and Pharmaceutical Dosage Forms: Disperse Systems, Volumes 1-2, edited by Lieberman et al; published by Marcel Dekker, Inc.

Compounds of this invention may be administered in any of the foregoing compositions and according to dosage regimens established in the art whenever treatment of disorders as described herein is required.

The daily dosage of the products may be varied over a wide range from 0.01 to 1,000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 300 mg/kg of body weight per day. Preferably, the range is from about 0.5 to about 5.0 mg/kg of body weight per day, most preferably, from about 1.0 to about 3.0 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

EXAMPLE 1

See Also Procedure as Described in JACS, 1989. Vol. 111, 4392-4398

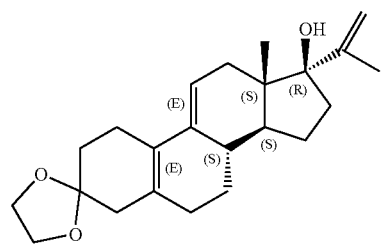

A freshly opened vial of $CeCl_3$ (5.0 g, 20 mmol) was transferred into a 250 mL round bottom flask. The resulting mixture was stirred at 140° C. for 4 hrs under high vacuum. An inert atmosphere was introduced into the flask while flask was still hot. The flask was then cooled down on an ice bath. THF (30 mL) was then added all at once with vigorous stirring. The ice bath was removed and the resulting suspension was stirred at ambient temperature for 16 hrs. Ethylene deltanone (3.14 g, 10 mmol) in THF (15 mL) was then added to the above suspension. The resulting mixture was stirred at room temperature for 1 hr and then cooled to 0° C. Isopropenyl magnesium bromide (15 mmol, 30 mL, 0.5 M in THF) was added with vigorous stirring. After 30 min, the reaction mixture was treated with sat. aqueous $NH_4Cl$ (60 mL). The product was extracted into EtOAc (3×50 mL). The combined extracts were washed with brine and aqueous $NaHCO_3$ solution, then with brine. The resulting mixture was then dried and concentrated, to yield the title compound as crude product as an off-white solid. This product was used in subsequent reactions without further purification.

$^1$H NMR ($CDCl_3$) δ 5.58 (s, 1H), 4.92 (s, 1H), 4.68 (s, 1H), 403 (s, 4H), 2.48-1.26 (m, 22H), 0.91 (s, 3H).

Ms: MH+ (357)

EXAMPLE 2

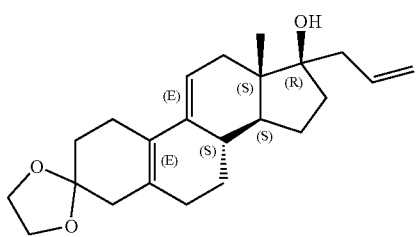

A solution of ethylene deltanone (6.28 g, 20.0 mmol) in THF (200 mL) was prepared. To this solution was added allylmagnesium bromide (1.0 M in ethyl ether, 44 mL, 44 mmol). The resulting solution turned from yellow to brown upon addition of allyl magnesium bromide, then back to yellow. The reaction mixture was stirred overnight under nitrogen at room temperature. Saturated ammonium chloride was then added, the reaction was mixture stirred, then ethyl acetate was added and the reaction mixture stirred. The layers were separated and the aqueous layer was extracted with ethyl acetate. The organic layers were dried over magnesium sulfate, filtered and evaporated to yield a residue. The residue was purified by column chromatography eluting with 0 to 10% ether/dichloromethane to yield the title compound as a residue.

1H NMR (400 MHz, CDCl3) δ 6.00 (m, 1H), 5.61 (s, 1H), 5.21-5.13 (m, 2H), 3.99 (s, 4H), 2.55-2.48 (s, 1H), 2.33-1.55 (m, 17H), 1.50-1.32 (m, 2H), 1.26-1.16 (m, 1H), 0.88 (s, 3H).

MH+=357, M+Na=378.9, MH(−water)=339

EXAMPLE 3

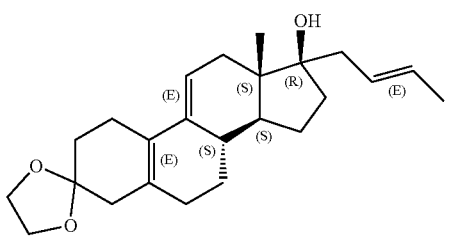

The title compound was prepared according to the procedure described in Example 2 above, starting from ethylene deltanone (5 g, 15.0 mmol). After silica gel column chromatograph (10% EtOAc/Hexane), the title compound product was obtained as an off-white solid.

1H NMR (CDCl3) δ 6.02 (m, 1H), 5.60 (s, 1H), 5.12 (d, 1H, J=5.6 Hz), 3.08 (s, 4H), 3.46 (s, 1H), 2.57-1.15 (m, 19H), 1.08 (d, 3H, J=7.0 Hz), 0.93 (s, 3H)

MS: MH+ (371), MNa+ (393)

EXAMPLE 4

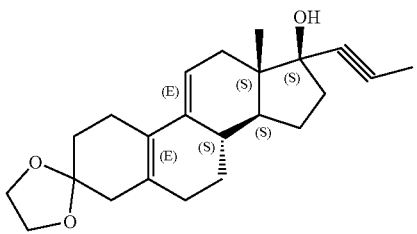

Ethylene deltanone (A) (7.13 g, 22.7 mmol) was dissolved in THF (120 mL) and 1-propynylmagnesium bromide (0.5M, 100 mL, 50 mmol) was added followed by additional THF (10 mL). The reaction mixture was stirred for 2 hours at room temperature, saturated ammonium chloride was added, and the reaction mixture extracted twice with ethyl acetate. The organic extracts were dried over magnesium sulfate, filtered, evaporated to yield the title compound as a brown solid. The product was used in subsequent reactions without further purification.

1H NMR (400 MHz, CDCl3) δ 5.62 (d, J=1.7 Hz, 1H), 3.99 (s, 4H), 2.66 (d, J=17.6 Hz, 1H), 2.56-2.51 (m, 1H), 2.28-1.68 (m, 17H), 1.43-1.20 (m, 3H), 0.82 (s, 3H)

MH+=355.2, MH(−water)=337.2

EXAMPLE 5

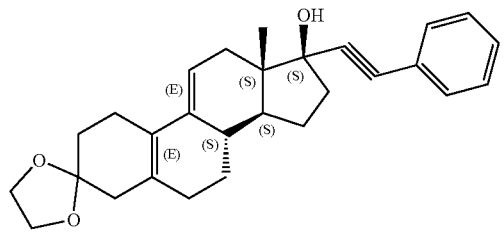

A solution of ethylene deltanone (A) (3.14 g, 10.0 mmol) in THF (60 mL) was prepared. To this solution was added phenylethynylmagnesium bromide (1.0M in ethyl ether, 25 mL, 25 mmol). The reaction mixture was stirred at room temperature under nitrogen. After 2 hours, additional phenylmagnesium bromide (5 mL) was added and the reaction was allowed to proceed overnight. Saturated ammonium chloride was then added and the reaction mixture was extracted three times with ethyl acetate. The organic layers were washed with water, brine, dried over magnesium sulfate, filtered and evaporated to yield a residue. The residue was purified by column chromatography (10 to 60% ethyl acetate/hexanes) to yield the title compound as a white solid.

1H NMR (400 MHz, CDCl3) δ 7.41-7.39 (m, 2H), 7.31-7.28 (m, 3H), 5.64 (t, J=2.57 Hz, 1H), 4.12 (s, 4H), 2.80-2.72 (d, J=17.7 Hz, 1H), 2.56-2.52 (m, 1H), 2.43-2.36 (m, 1H), 2.28-1.75 (m, 14H), 1.49-1.40 (m, 1H), 1.31-1.22 (m, 1H), 0.90 (s, 3H)

MH+=417.1, M+Na=439.2, MH(−water)=399.3

EXAMPLE 6

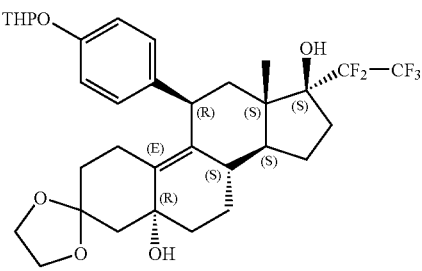

At −78° C., 1,1,1,2,2-pentafluoro-2-iodoethane (1.9 mL, 16 mmol) was condensed. A solution of 3,3-ethylenedioxy-5a,17b-dihydroxy-11b-[4-(2-tetrahydro-2-H-pyranoxy)-phenyl]-19-nor-17a-pregn9-ene-21-pentafluoroethane (1.028 g, 1.87 mmol) in diethyl ether (19 mL) was added at −78° C. A 1.5 M solution of CH3Li—LiBr complex in diethyl ether (8.7 mL, 13 mmol) was then added slowly, keeping the internal temperature below −6° C. The reaction mixture was stirred for 1 h at −78° C. The reaction mixture was then poured into saturated aqueous sodium bicarbonate solution. The aqueous layer was extracted with ethyl acetate. The organic portions were combined, washed with brine, dried over sodium sulfate, filtered, and evaporated to yield a residue. Chromatography of the residue over silica gel using hexane/ethylacetate (1:1) yielded the title compound as white solid.

1H NMR (CDCl3) δ 7.08 (d, 2H, J=9.1 Hz), 6.92 (d, 2H, J=9.1 Hz), 5.38 (broad s, 1H), 4.41-3.52 (m, 7H), 2.42-1.62 (m, 24H), 0.52 (d, 3H, J=5.1 Hz).

MS: 611 (M−18)H+.

EXAMPLE 7

3,3-[2-Ethanediylbis(oxy)]-5α,10α-oxidoestr-9(11)-en-17-one

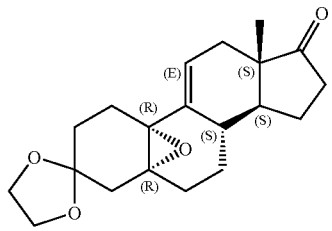

A solution of ethylene deltanone (4.0 g, 12.74 mmol) in 100 mL of dichloromethane was prepared and sodium bicarbonate (6.31 g, 75.17 mmol) was added. The resulting mixture was cooled to less than −40° C. and mCPBA (75%, 3.37 g, 14.65 mmol) in DCM (30 mL) was added in portions via syringe. The mCPBA was rinsed in the flask with DCM (10 mL) and then the reaction mixture was stirred for 30 minutes in an ice bath. Water was added and the reaction mixture was stirred. The layers were separated and the aqueous layer was extracted with dichloromethane. The organic layers were washed with saturated sodium bicarbonate solution, brine, dried over magnesium sulfate, filtered, evaporated to yield a yellow oil. The oil later solidified and was then dissolved in dichloromethane and purified by column chromatography eluting with 30-50% ethyl acetate/hexane in a gradient fashion to yield the title compound as a white solid.

$^1$H NMR (400 MHz, CDCl$_3$) δ 6.06 (br s, 1H), 3.97-3.88 (m, 4H), 2.50-2.45 (m, 2H), 2.19-1.22 (m, 16H), 0.88 (s, 3H) MH+=331

EXAMPLE 8

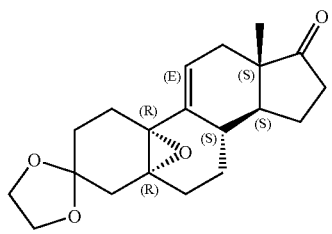

Trituration, Large Scale Procedure:

A solution of ethylene deltanone (30 g, 95.54 mmol) in DCM (600 mL) was prepared and sodium bicarbonate (47.4 g, 563.69 mmol) was added. The resulting mixture was cooled to less than −40° C. in a bath of acetone with some dry ice and mCPBA (75%, 3.37 g, 14.65 mmol). The temperature of the cooling bath was allowed to warm to 0° C. over 1 hour. Water was added and the layers were separated. The aqueous layer was extracted with dichloromethane. The organic layers were washed with water, brine, dried over magnesium sulfate, filtered, and evaporated to dryness. The resulting sticky oil was dissolved in diethyl ether (100 mL) and was then evaporated to a foam solid. Diethyl ether (100 mL) was added to the foam. Most of foam was dissolved, then the solvent was evaporated. Another portion of diethyl ether (100 mL) was added and stirred. White solid started to precipitate out, the mixture was stirred vigorously then stored in the cold room at 0° C. overnight. The white solid was filtered and washed with cold diethyl ether and dried on the vacuum funnel over 3 days. The title compound was obtained as a residue. TLC indicated the presence of title compound and a small amount of side product. The title compound was used in subsequent reactions without further purification.

$^1$H NMR (400 MHz, CDCl$_3$) δ 6.06 (br s, 1H), 3.97-3.88 (m, 4H), 2.50-2.45 (m, 2H), 2.19-1.22 (m, 16H), 0.88 (s, 3H). MH+=331

EXAMPLE 9

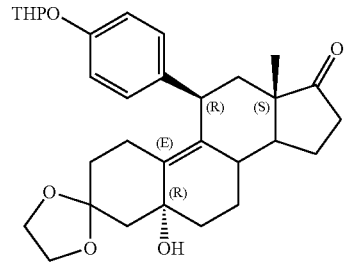

To a round-bottom flask containing copper (I) chloride (2.3 g, 23.03 mmol) under nitrogen was added 4-(2-tetrahydro-2-H-pyranoxy)-phenylmagnesium bromide (0.5M in THF) (100 mL, 50 mmol). The reaction mixture was stirred rapidly as it became white, thick, and exothermic. To the reaction mixture was then added 3,3-ethylenedioxy-5a,10a-epoxyestr-9,11-en-17-one (6.34 g, 19.19 mmol) and stirred for 2 hours. Saturated ammonium chloride was added and the reaction mixture was extracted three times with ethyl acetate. The organic extracts were washed with brine, dried over magnesium sulfate, filtered, evaporated to yield a residue. The residue was purified by column chromatography eluting with 20 to 95% ethyl acetate/hexanes to yield the title compound as a white solid.

$^1$H NMR (400 MHz, CDCl$_3$) δ 7.11 (d, J=8.6 Hz, 2H), 6.93(d, J=8.6 Hz, 2H), 5.36-5.31 (m, 1H), 4.37 (d, J=3.9 Hz, 1H), 4.27 (d, J=6.0 Hz, 1H), 4.04-3.89 (m, 5H), 3.63-3.59 (m, 1H), 2.46-2.29 (m, 5H), 2.11-1.98 (m, 5H), 1.89-1.80 (m, 5H), 1.70-1.51 (m, 7H), 1.29-1.24 (m, 2H), 0.88 (s, 3H).

M+Na=531.2. MH(−water)=491

EXAMPLE 10

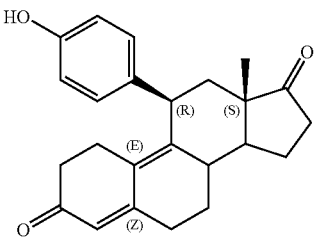

3,3-Ethylenedioxy-5a-hydroxy-11b-[4-(2-tetrahydro-2-H-pyranoxy)-phenyl]-estr-9-en-17-one (7.13 g, 14.02 mmol) was dissolved in acetone (300 mL). Oxalic acid (3.53 g, 28.03 mmol) in water (65 mL) was then added. The reaction mixture was stirred at 60° C. for 1.5 h. Water and EtOAc (100 mL/100 mL) were added. The aqueous layer was extracted with EtOAc (3×100 mL). The combined organic layers were dried and concentrated to yield a crude product. The crude product was purified by silica gel column (EtOAc) to yield the title compound as a white solid.

$^1$H NMR (400 MHz, CDCl$_3$) δ 7.02 (d, J=8.5 Hz, 2H), 6.76 (d, J=8.6 Hz, 2H), 5.82 (s, 1H), 4.36 (d, J=6.9 Hz, 1H), 2.76-2.72 (s, 1H), 2.65-2.62 (m, 2H), 2.52-2.31 (m, 5H), 2.18-1.88 (m, 5H), 1.63-1.52 (m, 4H), 0.57 (s, 3H)
MH+=363.1, M+Na=385.1. MH−=361.2

EXAMPLE 11

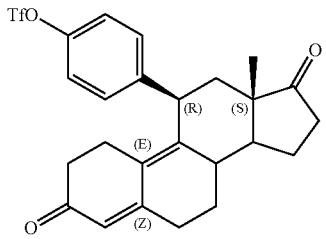

3,3-Ethylenedioxy-5α-hydroxy-11β-(4-hydroxy-phenyl)-estr-9-en-17-one (5.81 g, 16.0 mmol) was dissolved in THF (280 mL) and cooled to −78° C. NaH (1.41 g, 35.2 mmol, 60% in mineral oil) was added in one portion. The resulting mixture was stirred 10 min at −78° C., then Tf$_2$N-phenyl (8.59 g, 24 mml) in THF (20 mL) was added. The dry-ice bath was removed and the reaction mixture was stirred at room temperature for 16 h. After quenching the reaction with water (100 mL), the reaction mixture was extracted with EtOAc (3×100 mL). The combined organic layers were dried and concentrated to yield a residue, which was purified by silica gel column (30-80% EtOAc/Hexane) to yield the title compound as an off-white solid.

$^1$H NMR (CDCl$_3$) δ 7.32~7.14 (m, 4H), 5.82 (s, 1H), 4.48 (d, 1H, J=7.14 Hz), 2.78~1.93 (m, 12H), 1.6 (m, 4H), 0.56 (S, 3H).

MS (m/e): 495 (MH$^+$), 517 (MNa$^+$).

EXAMPLE 12

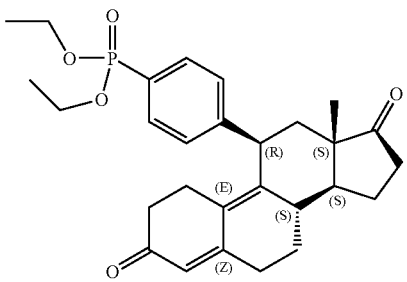

A mixture of 3,3-ethylenedioxy-5α-hydroxy-11β-(4-trifluoromethanesulfonyloxy)-estr-9-en-17-one (500 mg, 1.01 mmol), diethyl phosphite (279 mg, 2.02 mmol), Pd(OAc)$_2$ (23 mg, 0.101 mmol), dppb (65 mg, 0.152 mmol), DIPEA (0.7 mL, 4.04 mmol) and 1,4-dioxane (12 mL) in a microwaveble tube was placed in a CEM microwave apparatus. The reaction mixture was irradiated in microwave at 150° C. for 30 mins. The reaction mixture was then partitioned between water/EtOAc (100 mL/100 mL). The aqueous layer was extracted with EtOAc (2×100 mL). The combined organic layers were washed with brine (200 mL), dried and concentrated to yield a residue which was purified by silica gel purification (0-15% MeOH/EtOAc) to yield the title compound as a yellow solid.

$^1$H NMR (CDCl$_3$) δ 7.75 (m, 2H), 7.28 (m, 2H), 5.81 (s, 1H), 4.48 (d, 1H, J=7.14 Hz), 4.15 (m, 4H), 2.78~1.93 (m, 16H), 1.33 (m, t, 6H, J=7.6 Hz), 0.55 (s, 3H).

MS (m/e): 483 (MH$^+$), 505 (MNa$^+$), 481 (MH$^-$).

EXAMPLE 13

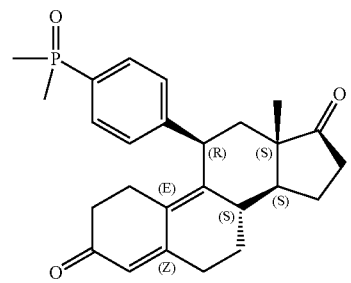

The title compound was prepared according to the procedure described in Example 12 above, and isolated as a residue.

$^1$H NMR (400 MHz, CDCl$_3$) δ 7.69-7.64 (m, 2H), 7.35-7.33 (m, 2H), 5.82 (s, 1H), 4.48 (d, J=7.2 Hz, 1H), 2.76-1.57 (m, 22H), 0.53 (s, 3H)

MH+=423.1, M+Na=445.2

EXAMPLE 14

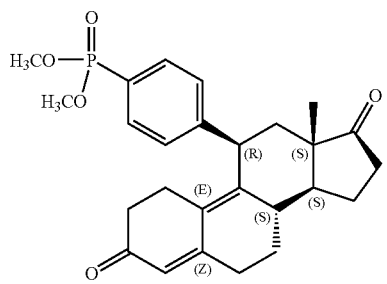

The title compound was prepared according to the procedure described in Example 12 above, and isolated as a residue.

$^1$H NMR (CDCl$_3$) δ 7.72 (m, 2H), 7.32 (m, 2H), 5.78 (s, 1H), 4.47 (d, 1H, J=7.0 Hz), 3.68 (s, 3H), 3.73 (s, 3H), 2.76~1.95 (m, 14H), 1.62 (m, 4H), 0.51 (s, 3H).

MS (m/e): 455 (MH$^+$), 477 (MNa$^+$), 481 (MH$^-$).

EXAMPLE 15

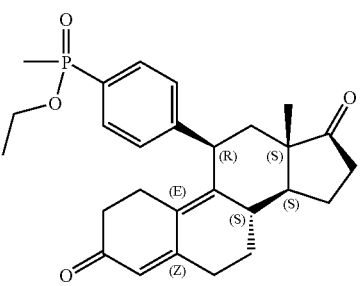

The title compound was prepared according to the procedure described in Example 12 above, and isolated as a residue.

$^1$H NMR (CDCl$_3$) δ 7.73 (m, 2H), 7.34 (m, 2H), 5.81 (s, 1H), 4.48 (d, 1H, J=7.0 Hz), 4.08 (m, 1H), 3.85 (m, 1H), 2.78~1.93 (m, 19H), 1.30 (t, 3H, J=7.1 Hz), 0.55 (s, 3H)

MS (m/e): 475 (MNa$^+$), 451 (MH$^-$).

EXAMPLE 16

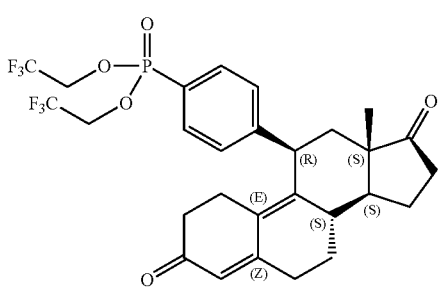

The title compound was prepared according to the procedure described in Example 12 above, and isolated as a residue.

$^1$H NMR (CDCl$_3$) δ 7.75 (m, 2H), 7.32 (m, 2H), 5.81 (s, 1H), 4.45 (m, 4H), 3.5 (s, 1H), 2.68~1.95(m, 16H), 0.50 (s, 3H).

MS (m/e): 591 (MH$^+$), 613 (MNa$^+$), 589 (MH$^-$).

EXAMPLE 17

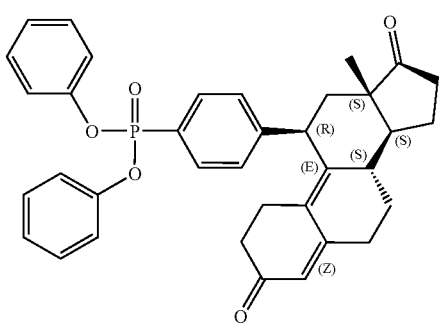

The title compound was prepared according to the procedure described in Example 12 above, and isolated as a residue.

$^1$H NMR (CDCl$_3$) δ 7.88 (m, 2H), 7.31 (m, 2H), 7.30~7.12 (m, 10H), 5.81 (s, 1H), 4.49 (d, 1H, J=7.0 Hz), 2.72~1.49 (m, 16H), 0.48 (s, 3H).

MS (m/e): 579 (MH$^+$), 601 (MNa$^+$), 577 (MH$^-$).

EXAMPLE 18

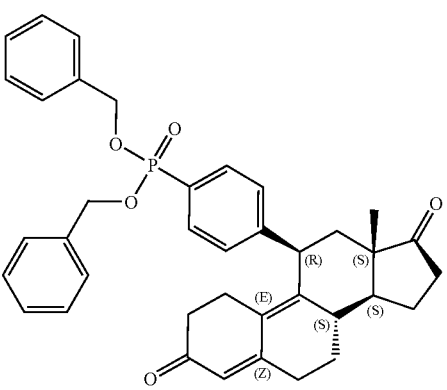

The title compound was prepared according to the procedure described in Example 12 above, and isolated as a residue.

$^1$H NMR (CDCl$_3$) δ 7.73 (m, 2H), 7.38~7.21 (m, 12H), 5.81 (s, 1H), 5.08 (m, 4H), 4.45 (d, 1H, J=7.0 Hz), 4.08 (m, 1H), 3.85 (m, 1H), 2.78~1.93 (m, 14H), 0.52 (s, 3H).

MS (m/e): 606 (MH$^+$), 629 (MNa$^+$), 605 (MH$^-$).

EXAMPLE 19

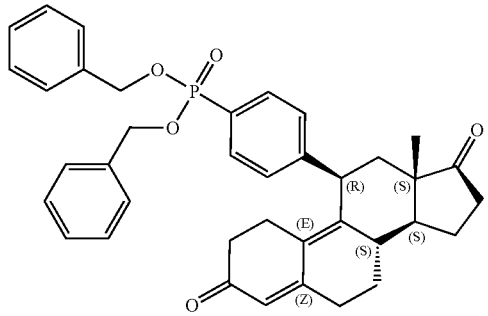

The title compound was prepared according to the procedure described in Example 12 above, and isolated as a residue.

$^1$H NMR (CDCl$_3$) δ 7.59~7.24 (m, 12H), 5.79 (s, 1H), 4.48 (d, 1H, J=7.0 Hz), 2.78 (m, 16H), 0.51 (s, 3H).

MS (m/e): 615, 617 (MH$^+$).

EXAMPLE 20

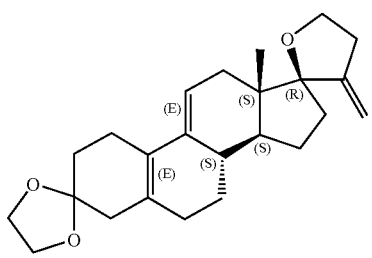

The title compound was synthesized from ethalene deltanone according to the procedure reported in Hamersma, J. A.; Orlemans, E. O. M.; Rewinkel, J.B.M. EP0582338A2.

EXAMPLE 21

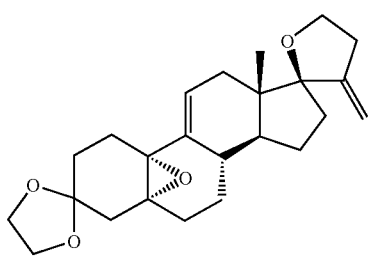

The title compound was prepared as a white solid according to the procedure described in Example 7 above, starting from 19,24-Dinorchola-5(10), 9(11), 20-trien-3-one, 17,23-epoxy-, cyclic 1,2-ethanediyl acetal, (17α)-(9Cl) (4.0 g, 10.85 mmol).

$^1$H NMR (400 MHz, CDCl$_3$) δ 5.96 (br s, 1H), 5.03 (s, 1H), 4.79 (s, 1H), 3.96-3.75 (m, 6H), 2.64-2.60 (m, 2H), 2.43 (m, 1H), 2.17-1.12 (m, 17H), 0.87 (s, 3H)

MH+=385

EXAMPLE 22

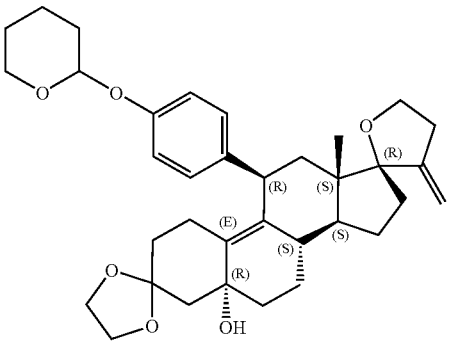

The title compound was prepared as a white solid according to the procedure as described in Example 9 above, starting from the compound prepared in Example 21 above (1.0 g, 2.60 mmol).

$^1$H NMR (400 MHz, CDCl$_3$) δ 7.07 (d, J=8.6 Hz, 2H), 6.92 (d, J=8.7 Hz, 2H), 5.34 (m, 1H), 5.08 (s, 1H), 4.82 (s, 1H), 4.35 (s, 1H), 4.15 (s, 1H), 4.0-3.89 (m, 5H), 3.81-3.76 (m, 2H), 3.60 (m, 1H), 2.63 (m, 2H), 2.40-1.24 (m, 24H), 0.53 (s, 3H).

M+Na=585, MH(—H$_2$O)=545

EXAMPLE 23

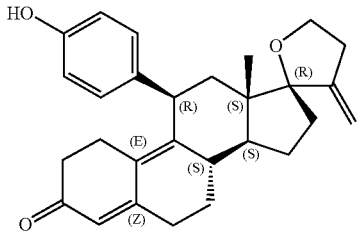

The title compound was prepared as a white solid according to the procedure in 10 above, starting from the compound prepared in Example 11 above (100 mg, 0.178 mmol).

$^1$H NMR (400 MHz, CDCl$_3$) δ 6.99 (d, J=8.5 Hz, 2H), 6.73 (dd, J=1.9 and 6.7 Hz, 2H), 5.77 (s, 1H), 5.44 (s, 1H), 5.13 (s, 1H), 4.84 (s, 1H), 4.23 (d, J=7.1 Hz, 1H), 3.87-3.80 (m, 2H), 2.69-1.24 (m, 18H), 0.59 (s, 3H)

M+Na=439, MH+=417

EXAMPLE 24

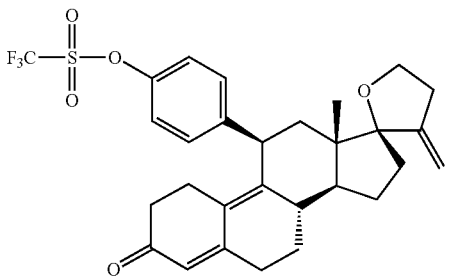

The title compound was prepared as a white solid according to the procedure in Example 11 above, starting from the compound prepared in Example 23 above, (100 mg, 0.178 mmol).

$^1$H NMR (400 MHz, CDCl$_3$) δ 7.26-7.18 (m, 4H), 5.79 (s, 1H), 5.15 (t, J=1.8 Hz, 1H), 4.86 (s, 1H), 4.32 (d, J=7.1, 1H), 3.87-3.77 (m, 2H), 2.72-2.56 (m, 5H), 2.48-1.24 (m, 13H), 0.54 (s, 3H)

M+Na=571, MH+=549

EXAMPLE 25

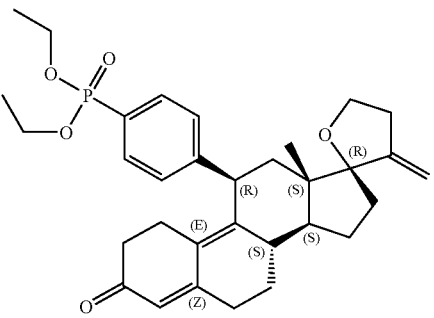

The title compound was prepared as a white solid according to the procedure in Example 12 above, starting from the compound prepared as in Example 24, above.

$^1$H NMR (400 MHz, CDCl$_3$) δ 7.72 (dd, J=8.2 and 12.0 Hz, 2H), 7.28-7.26 (m, 2H), 5.78 (s, 1H), 5.14 (s, 1H), 4.86 (s, 1H), 4.34 (d, J=7.3 Hz, 1H), 4.17-4.05 (m, 4H), 3.85-3.79 (m, 2H), 2.70-2.58 (m, 5H), 2.49-1.24 (m, 19H), 0.53 (s, 3H)

M+Na=559, MH+=536

EXAMPLE 26

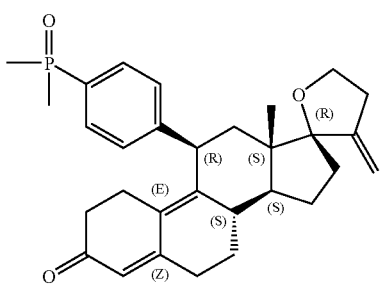

The title compound was prepared as a white solid according to the procedure in Example 12 above, starting from 19,24-dinorchola-4,9,20-trien-3-one, 17,23-epoxy-11-(4-trifluoromethanesulfonyloxyphenyl)-, (11β,17α)-(9CI), the compound prepared as in Example 24, above $^1$H NMR (400 MHz, CDCl$_3$) δ 7.67-7.61 (dd, J=8.5 and 11.4 Hz, 2H), 7.31-7.26 (dd, J=2.0 and 8.3 Hz, 2H), 5.78 (s, 1H), 5.15 (t, J=1.8 Hz, 1H), 4.86 (s, 1H), 4.34 (d, J=7.0 Hz, 1H), 3.85-3.79 (m, 2H), 3.49 (m, 1H), 2.73-2.53 (m, 5H), 2.49-0.80 (m, 18H), 0.55 (s, 3H)

M+Na=477, MH+=500

EXAMPLE 27

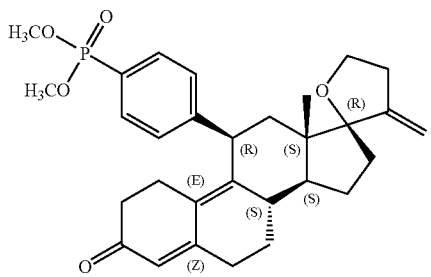

The title compound was prepared as a white solid according to the procedure in Example 12 above, starting from 19,24-dinorchola-4,9,20-trien-3-one, 17,23-epoxy-11-(4-trifluoromethanesulfonyloxyphenyl)-, (11β,17α)-(9Cl), the compound prepared as in Example 24, above $^1$H NMR (400 MHz, CDCl$_3$) δ 7.71 (m, 2H), 7.21 (m, 2H), 5.71 (s, 1H), 5.12 (s, 1H), 4.81 (s, 1H), 4.31 (d, 1H), 3.75 (m, 8H), 3.5 (s, 1H), 2.68~1.38 (m, 17H), 0.52 (s, 3H)

M+Na=531, MH+=509, 2 MH+ (1017).

EXAMPLE 28

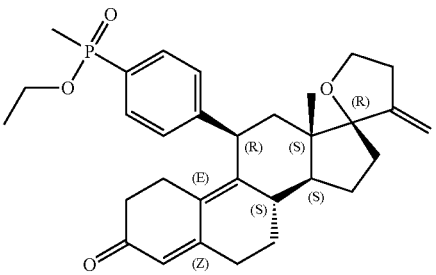

The title compound was prepared as a white solid according to the procedure in Example 12 above, starting from 19,24-dinorchola-4,9,20-trien-3-one, 17,23-epoxy-1-(4-trifluoromethanesulfonyloxyphenyl)-, (11β,17α)-(9Cl), the compound prepared as in Example 24, above $^1$H NMR (400 MHz, CDCl$_3$) δ 7.72 (m, 2H), 7.29 (m, 2H), 5.79 (s, 1H), 5.18 (s, 1H), 4.86 (s, 1H), 4.36 (d, 1H), 4.08 (m, 2H), 3.82 (m, 2H), 3.4 (s, 1H), 2.71~1.22 (m, 23H), 0.52 (s, 3H)

M+Na=507, MH+=529.

EXAMPLE 29

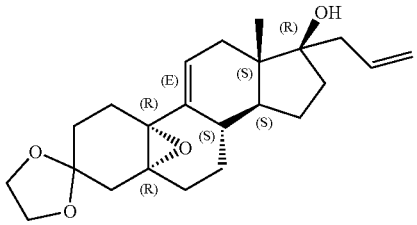

The title compound was prepared as a white solid according to the procedure as described in Example 7 above, starting from the compound prepared as in Example 2, above.

MH+=373 $^1$H NMR (400 MHz, CDCl$_3$) δ 6.08-6.06 (m, 1H), 6.00-5.94 (m, 1H), 5.21-5.13 (m, 2H), 3.96-3.87 (m, 4H), 2.51-2.46 (s, 1H), 2.30-1.11 (m, 20H), 0.89 (s, 3H)

EXAMPLE 30

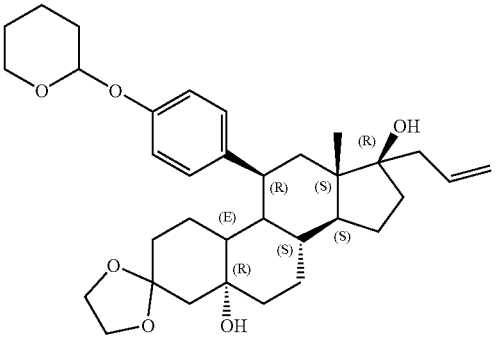

Procedure A: (CuCl, Grignard; C17 Side Chain Already Installed, C11 Side Chain Installed Second)

The title compound was prepared as a white solid according to the procedure as described in Example 9, above, starting from the compound prepared as in Example 29 above.

Procedure B: (Allyl MqBr Addition; C11 Side Chain Installed First; C17 Side Chain Installed Second)

A solution of the compound prepared as in Example 9 above, (0.65 g, 1.28 mmol) in THF (20 mL). To this solution was added allylmagnesium bromide (1.0M in ethyl ether, 5.11 mL, 5.11 mmol) and the reaction stirred at room temperature for 2 hours. Saturated ammonium chloride was then added and the reaction mixture extracted twice with ethyl acetate. The organic layers were washed with brine, dried over magnesium sulfate, filtered and evaporated to yield the title compound as a white solid. This product was used in subsequent reactions without further purification.

$^1$H NMR (400 MHz, CDCl$_3$) δ 7.10 (d, J=8.6 Hz, 2H), 6.92 (dd, J=1.4 and 8.6 Hz, 2H), 6.03-5.93 (m, 1H), 5.36-5.32 (m, 1H), 5.20-5.10 (m, 2H), 4.38 (d, J=4.5 Hz, 1H), 4.27 (d, J=5.6 Hz, 1H), 4.05-3.88 (m, 4H), 3.63-3.58 (m, 1H), 2.48-1.24 (m, 28H), 0.50 (s, 3H).

M+Na=573.5, MH(–water)=533.4

EXAMPLE 31

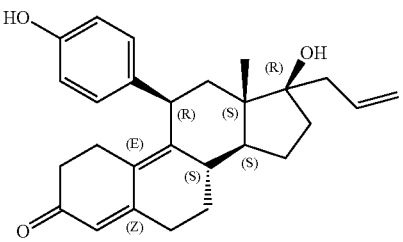

The title compound was prepared as a white solid according to the procedure as described in Example 10 above, starting from the compound prepared as in Example 30 above.

$^1$H NMR (400 MHz, CDCl$_3$) δ 7.00 (d, J=8.5 Hz, 2H), 6.73 (d, J=8.6 Hz, 2H), 6.04-5.93 (m, 1H), 5.79 (s, 1H), 5.24-5.16 (m, 2H), 2.75-2.69 (m, 1H), 2.60-2.57 (m, 2H), 2.52-1.33 (m, 18H), 0.57 (s, 3H)

MH+=405

EXAMPLE 32

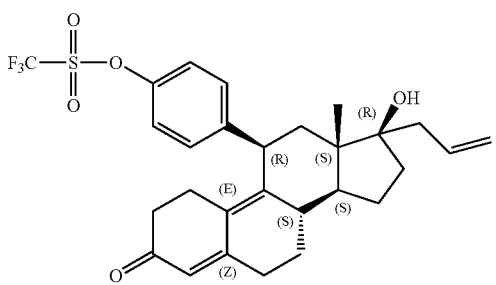

The title compound was prepared as a white solid according to the procedure described in Example 12, above, starting from the compound prepared as in Example 31 (216 mg, 0.53 mmol). The title compound was obtained as white solid.

$^1$H NMR (400 MHz, CDCl$_3$) δ 7.27 (d, J=7.7 Hz, 2H), 7.19 (d, J=8.8 Hz, 2H), 6.03-5.93 (m, 1H), 5.80 (s, 1H), 5.25-5.17 (m, 2H), 4.44 (d, J=6.7 Hz, 1H), 2.77-2.70 (m, 1H), 2.62-2.58 (m, 2H), 2.52-2.20 (m, 7H), 2.11-1.95 (m, 3H), 1.71-1.32 (m, 6H), 0.52 (s, 3H).

MH+=536.8, M+Na=558.8

EXAMPLE 33

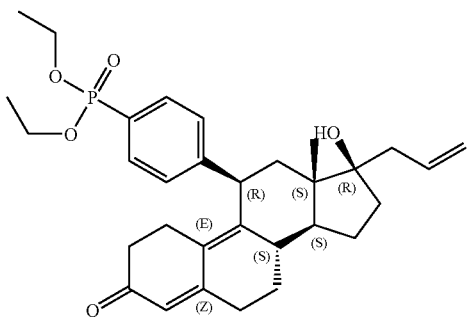

The title compound was prepared according to the procedure described in Example 12, above starting from the compound prepared as in Example 31 above (47 mg, 0.0868 mmol). The title compound was obtained as a whitel solid.

MH+=525.3, M+Na=547. $^1$H NMR (400 MHz, CDCl$_3$) δ 7.72 (dd, J=8.2 and 12.9 Hz, 2H), 7.30 (dd, J=3.6 and 8.2 Hz, 2H), 6.03-5.91 (m, 1H), 5.79 (s, 1H), 5.28-5.17 (m, 2H), 4.46 (d, J=6.9 Hz, 1H), 4.17-4.07 (m, 4H), 2.74-2.68 (m, 1H), 2.70-1.25 (m, 24H), 0.52 (s, 3H).

EXAMPLE 34

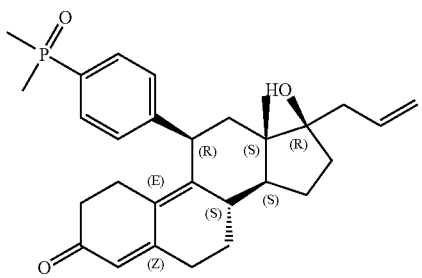

The compound was prepared according to the procedure in Example 12 above, starting from the compound prepared as in Example 31 above, (50 mg, 0.093 mmol). The title compound was obtained as white solid, as a mixture of rotamers.

MH+=465.3, M+Na=487.2. $^1$H NMR (400 MHz, CDCl$_3$) δ 7.66-7.60 (m, 2H), 7.34-7.27 (m, 2H), 6.03-5.93 (m, 0.7H), 5.79 (s, 1H), 5.65 (m, 0.3H), 5.24-5.16 (m, 2H), 4.46 (d, J=6.8 Hz, 0.7H), 4.39 (d, J=7.1 Hz, 0.3H), 2.75-2.69 (m, 1H), 2.60-2.58 (m, 2H), 2.50-1.24 (m, 22H), 0.53 (s, 3H).

EXAMPLE 35

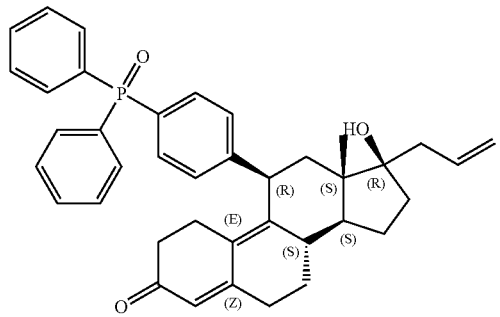

The compound was prepared according to the procedure in Example 12 above, starting from the compound prepared as in Example 31 above, (100 mg, 0.186 mmol). The title compound was obtained as white solid.

MH+=588.9. $^1$H NMR (400 MHz, CDCl$_3$) δ 7.67-7.61 (m, 4H), 7.58-7.43 (m, 8H), 7.31-7.28 (m, 2H), 6.03-5.93 (m, 1H), 5.77 (s, 1H), 5.25-5.16 (m, 2H), 4.46 (d, J=7.0 Hz, 1H), 2.76-2.70 (m, 1H), 2.58-1.33 (m, 18H), 0.54 (s, 3H).

EXAMPLE 36

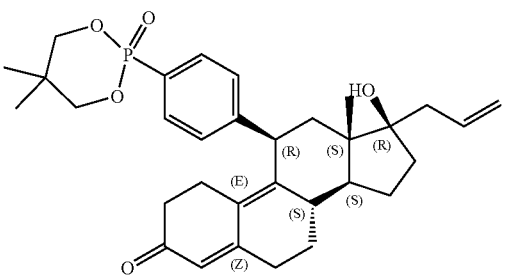

The compound was prepared according to the procedure in Example 12 above, starting from the compound prepared as in Example 31 above, (100 mg, 0.186 mmol). The title compound was obtained as white solid.

MH+=536.8. $^1$H NMR (400 MHz, CDCl$_3$) δ 7.76 (dd, J=8.1 and 13.2 Hz, 2H), 7.32 (dd, J=3.6 and 7.6 Hz, 2H), 5.78 (s, 1H), 5.69-5.58 (m, 2H), 4.40-4.27 (m, 3H), 3.88-3.79 (m, 2H), 2.74-2.66 (m, 1H), 2.60-2.58 (m, 2H), 2.47-1.20 (m, 17H), 1.17 (s, 3H), 1.08 (s, 3H), 0.52 (s, 3H).

EXAMPLE 37

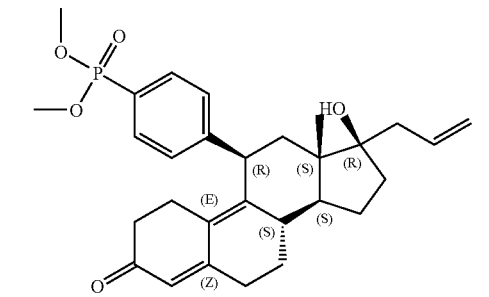

The compound was prepared according to the procedure in Example 12 above, starting from the compound prepared as in Example 31 above (200 mg, 0.373 mmol). The title compound was obtained as white solid.

MH+=497.2, M+Na=519.3 ¹H NMR (400 MHz, CDCl₃) δ 7.74-7.67 (m, 2H), 7.33-7.28 (m, 2H), 6.03-5.93 (m, 1H), 5.79 (s, 1H), 5.28-5.17 (m, 2H), 3.77 (s, 3H), 3.75 (s, 3H), 2.75-2.69 (m, 1H), 2.60 (m, 2H), 2.53-1.25 (m, 17H), 0.52 (s, 3H).

EXAMPLE 38

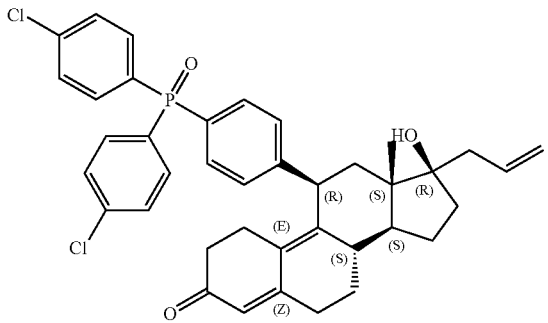

The compound was prepared according to the procedure in Example 12 above, starting from the compound prepared as in Example 31 above (200 mg, 0.373 mmol). The title compound was obtained as white solid as a mixture rotamers.

MH+=657.2, MH−=655.0, M+Na=679.0 ¹H NMR (400 MHz, CDCl₃) δ 7.59-7.44 (m, 10H), 7.33-7.29 (m, 2H), 6.01-5.94 (m, 0.4H), 5.78 (d, J=3.7 Hz, 1H), 5.64-5.58 (m, 0.6H), 5.25-5.17 (m, 1H), 4.47 (d, J=7.1 Hz, 0.4H), 4.40 (d, J=7.2 Hz, 0.6H), 2.76-2.68 (m, 1H), 2.56 (m, 2H), 2.48-1.34 (m, 17H), 0.53 (s, 3H).

EXAMPLE 39

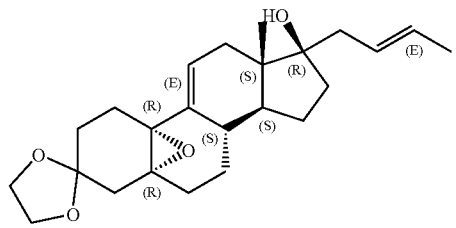

The title compound was prepared according to the procedure in Example 7, above, starting from the compound prepared as in Example 3, (1.95 g, 5.26 mmol). The title compound was obtained as white solid, as a mixture of rotamers

EXAMPLE 40

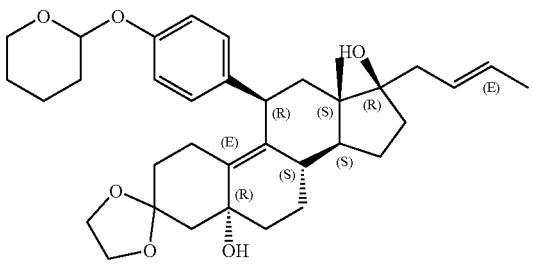

The compound was prepared according to the procedure in Example 9, starting from the compound prepared as in Example 39 above, (1.27 g, 3.29 mmol). The title compound was obtained as off-white solid, as a mixture of rotamers.

M+Na=587. ¹H NMR (400 MHz, CDCl₃) δ 7.09 (d, J=8.6 Hz, 2H), 6.91 (dd, J=1.5 and 8.7 Hz, 2H), 6.08-6.00 (m, 0.5H), 5.95-5.86 (m, 0.5H), 5.35-5.32 (m, 0.5H), 5.15-5.08 (m, 2.5H), 4.37 (d, J=3.9 Hz, 0.5H), 4.24 (d, J=6.4 Hz, 0.5H), 4.04-3.84 (m, 4H), 3.62-3.58 (m, 0.5H), 3.45 (d, J=5.4 Hz, 0.5H), 2.53-0.91 (m, 31H), 0.50 (d, J=1.9 Hz, 3H).

EXAMPLE 41

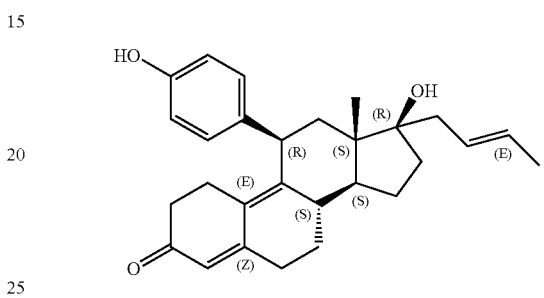

The title compound was prepared according to the procedure in Example 10 above, starting from the compound prepared as in Example 40 above, (585 mg, 1.04 mmol). The title compound was obtained as white solid.

MH+=419. ¹H NMR (400 MHz, CDCl₃) δ 7.02-7.00 (d, J=8.4 Hz, 2H), 6.74-6.71 (d, J=8.6 Hz, 2H), 6.08-5.98 (m, 1H), 5.77 (s, 1H), 5.43 (s, 1H), 5.17-5.13 (m, 2H), 4.34 (d, J=6.9 Hz, 1H), 2.75-2.69 (m, 1H), 2.59-2.00 (m, 11H), 1.76 (s, 1H), 1.68-1.56 (m, 3H), 1.46-1.33 (m, 2H), 1.16 (d, J=6.8 Hz, 3H), 0.58 (s, 3H).

EXAMPLE 42

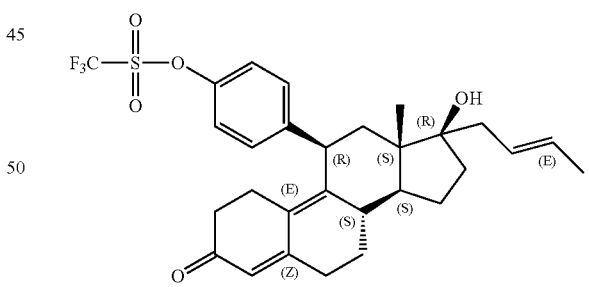

The title compound was prepared according to the procedure in Example 11 above, starting from the compound prepared as in Example 41 above, (119 mg, 0.284 mmol). The title compound was obtained as white solid.

MH+=551.1 ¹H NMR (400 MHz, CDCl₃) δ 7.29 (d, J=8.0 Hz, 2H), 7.18 (d, J=8.8 Hz, 2H), 6.06-5.97 (m, 1H), 5.79 (s, 1H), 5.17-5.14 (m, 2H), 4.43 (d, J=6.0 Hz, 1H), 2.76-2.70 (m, 1H), 2.60-2.02 (m, 11H), 1.71-1.36 (m, 6H), 1.16 (d, J=6.8 Hz, 3H), 0.52 (s, 3H).

EXAMPLE 43

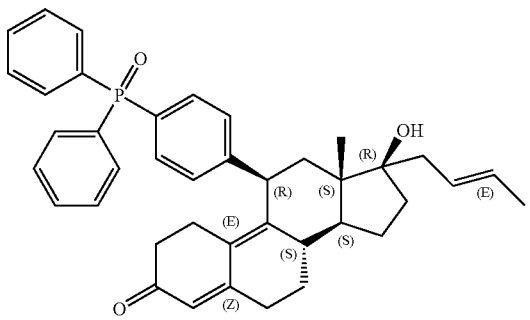

The title compound was prepared according to the procedure in Example 12 above, starting from the compound prepared as in example 42 above (30 mg, 0.054 mmol). The title compound product was obtained as white solid.

MH+=603.2 $^1$H NMR (400 MHz, CDCl$_3$) δ 7.74-7.45 (m, 12H), 7.30-7.28 (m, 2H), 6.06-5.97 (s, 1H), 5.76 (s, 1H), 5.17-5.13 (m, 2H), 4.45 (d, J=6.5 Hz, 1H), 2.75-2.69 (m, 1H), 2.58-1.15 (m, 20H), 0.54 (s, 3H).

EXAMPLE 44

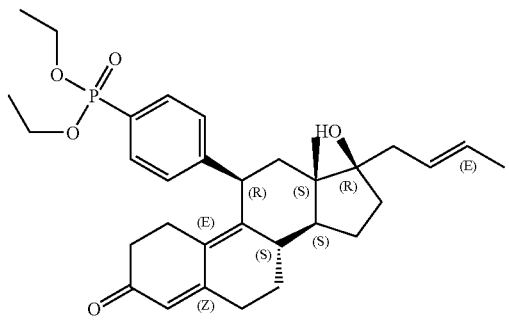

The title compound was prepared according to the procedure in Example 12 above, starting from the compound prepared as in Example 42 above (30 mg, 0.054 mmol). The title compound was obtained as white solid.

MH+=539.2, M+Na=561.2. $^1$H NMR (400 MHz, CDCl$_3$) δ 7.73-7.68 (m, 2H), 7.30-7.27 (m, 2H), 6.07-5.98 (m, 1H), 5.79 (s, 1H), 5.17-5.14 (m, 2H), 4.44 (d, J=6.8 Hz, 1H), 4.16-4.03 (m, 4H), 2.74-2.68 (m, 1H), 2.61-2.56 (m, 2H), 2.52-2.23 (m, 7H), 2.10-2.03 (m, 2H), 1.73-1.55 (m, 4H), 1.48-1.36 (m, 2H), 1.33-1.25 (m, 6H), 1.16 (d, J=6.8 Hz, 3H), 0.52 (s, 3H).

EXAMPLE 45

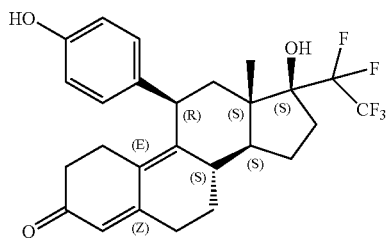

The title compound was prepared according to the procedure in Example 10 above, starting from the compound prepared as in Example 6 above (236 mg, 0.37 mmol). The title compound was obtained as white solid.

MH+=483.1 $^1$H NMR (400 MHz, CDCl$_3$) δ 7.00 (d, J=8.5 Hz, 2H), 6.74 (d, J=8.6 Hz, 2H), 5.88 (s, 1H), 5.80 (s, 1H), 4.37 (d, J=6.6 Hz, 1H), 2.77-2.24 (m, 10H), 2.09-2.01 (m, 2H), 1.84-1.76 (m, 3H), 1.56-1.40 (m, 2H), 0.62 (s, 3H).

EXAMPLE 46

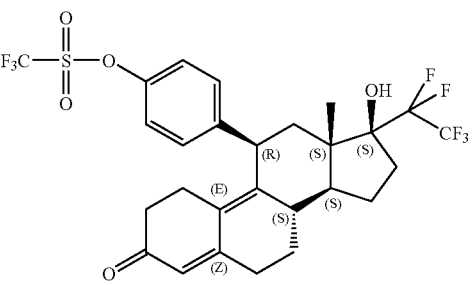

The title compound was prepared according to the procedure in Example 11 above, starting from the compound prepared as in Example 45 above (105 mg, 0.218 mmol). The title compound was obtained as white solid.

MH+=615.2, M+Na=637.0 $^1$H NMR (400 MHz, CDCl$_3$) δ 7.29-7.26 (m, 2H), 7.21 (d, J=8.9 Hz, 2H), 5.81 (s, 1H), 4.47 (d, J=6.3 Hz, 1H), 2.77-2.70 (m, 1H), 2.61-2.23 (m, 10H), 2.10-2.02 (m, 1H), 1.83-1.75 (m, 3H), 1.55-1.43 (m, 2H), 0.57 (s, 3H).

EXAMPLE 47

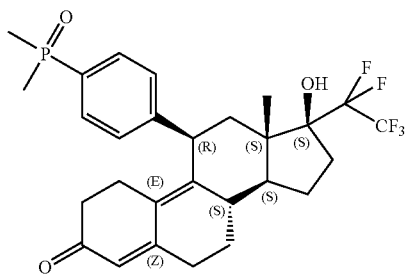

The title compound was prepared according to the procedure in Example 12 above, starting from the compound prepared as in Example 46 above (50 mg, 0.08 mmol). The title compound was obtained as white solid.

MH+=543.2, M+Na=565.2 $^1$H NMR (400 MHz, CDCl$_3$) δ 7.68-7.63 (m, 2H), 7.39 (dd, J=1.8 Hz and 8.0 Hz, 2H), 5.80 (s, 1H), 4.50 (d, J=7.0 Hz, 1H), 2.82-2.72 (m, 1H), 2.64-2.20 (m, 10H), 1.85-1.43 (m, 10H), 1.58-1.40 (m, 2H), 0.60 (s, 3H).

EXAMPLE 48

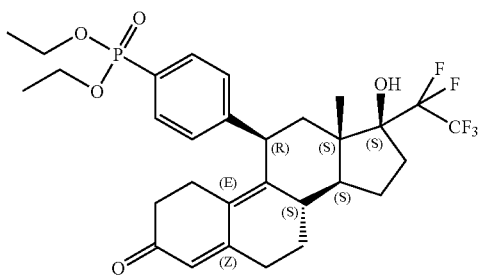

The title compound was prepared according to the procedure in Example 12 above, starting from the compound prepared as in Example 46 above (23 mg, 0.0374 mmol). The title compound was obtained as white solid.

MH+=603.2, M+Na=625.2 $^1$H NMR (400 MHz, CDCl$_3$) δ 7.73 (dd, J=8.1 and 12.9 Hz, 2H), 7.34 (dd, J=3.5 and 7.7 Hz, 2H), 5.80 (s, 1H), 4.49 (d, J=6.8 Hz, 1H), 4.16-4.02 (m, 4H), 2.76-1.26 (m, 23H), 0.58 (s, 3H).

EXAMPLE 49

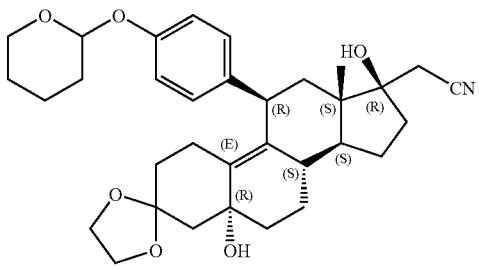

In a round-bottom flask was added THF (12 mL) and was cooled using a dry ice-acetone bath under nitrogen. Next, n-butyllithium was added (2.5M, 1.6 mL, 4 mmol) followed by acetonitrile (0.35 mL, 6.7 mmol). The reaction mixture was stirred for 30 minutes during which time the reaction mixture became orange. A solution of the compound prepared as in Example 9 (3,3-Ethylenedioxy-5a-hydroxy-11b-[4-(2-tetrahydro-2-H-pyranoxy)-phenyl]-estr-9-en-17-one) (700 mg, 1.376 mmol) in THF (5 mL) was added and the reaction mixture became thick and hard to stir. The reaction mixture was stirred in a dry-ice acetone bath for 15 minutes, then warmed to room temperature. Saturated ammonium chloride and water were added and the reaction mixture was extracted twice with ethyl acetate. The organic extracts were dried over magnesium sulfate, filtered, and evaporated. The residue was purified by column chromatography eluting with 10 to 40% ethyl acetate/hexanes and then with ethyl acetate to make sure all product was eluted. The title compound was obtained as white solid.

M+Na=572.3, MH(−water)=532.3. $^1$H NMR (400 MHz, CDCl$_3$) δ 7.09 (d, J=8.6 Hz, 2H), 6.93 (dd, J=1.3 and 8.7 Hz, 2H), 5.36-5.32 (m, 1H), 4.40 (d, J=4.6 Hz, 1H), 4.28 (d, J=6.1 Hz, 1H), 4.04-3.90 (m, 6H), 3.62-3.59 (m, 1H), 2.64-1.24 (m, 26H), 0.52 (d, J=1.3 Hz, 3H).

EXAMPLE 50

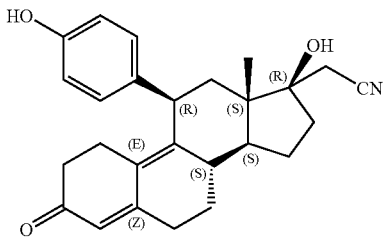

The title compound was prepared according to the procedure in Example 10 above, starting from the compound prepared as in Example 49 (440 mg, 0.80 mmol). The title compound was obtained as white solid.

MH+=404.2 $^1$H NMR (400 MHz, MeOD) δ 7.03 (d, J=8.5 Hz, 2H), 6.70 (d, J=8.7 Hz, 2H), 5.73 (s, 1H), 4.42 (d, J=7.4 Hz, 1H), 2.81-1.29 (m, 20H), 0.59 (s, 3H),

EXAMPLE 51

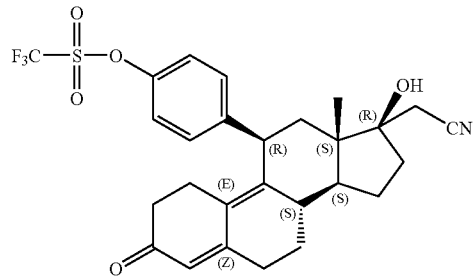

The title compound was prepared according to the procedure in Example 11 above, starting from the compound prepared as in Example 50 above, (78 mg, 0.193 mmol). The title compound was obtained as white solid.

MH+=536.2, M+Na=558.2. $^1$H NMR (400 MHz, CDCl$_3$) δ 7.28-7.20 (m, 4H), 5.81 (s, 1H), 4.48 (d, J=7.0 Hz, 1H), 2.75-2.30 (m, 10H), 2.12-2.05 (m, 2H), 1.95-1.77 (m, 4H), 1.47-1.42 (m, 3H), 0.55 (s, 3H).

EXAMPLE 52

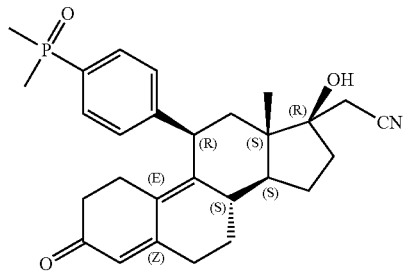

The title compound was prepared according to the procedure in Example 12 above, starting from the compound prepared as in Example 51 3,3-ethylenedioxy-5a-17b-dihydroxy-11b-[4-(trifluoromethanesulfonyloxy)phenyl]-19-nor-17α-pregn-9-ene-21-carbonitrile (66 mg, 0.123 mmol). The title compound was obtained as white solid.

MH+=464.2 $^1$H NMR (400 MHz, CDCl$_3$) δ 7.65 (dd, J=8.3 Hz and 11.3 Hz, 2H), 7.32 (dd, J=2.0 Hz and 8.1 Hz, 2H), 5.81 (s, 1H), 4.49 (d, J=7.1 Hz, 1H), 2.75-2.27 (m, 12H), 2.13-2.05 (m, 2H), 1.95-1.87 (m, 2H), 1.74 (s, 3H), 1.71 (s, 3H), 1.50-1.40 (m, 3H), 0.56 (s, 3H).

EXAMPLE 53

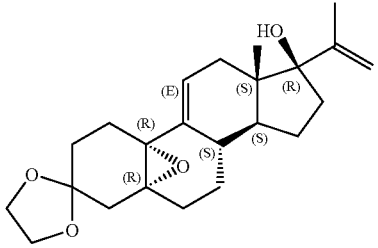

This title compound was prepared according to procedure in Example 47 above, starting from the compound prepared as in Example 1 above (2.8 g, 7.85 mmol). The title compound was obtained as white solid.

MH+=373.2, MH(−water)=355.2 $^1$H NMR (400 MHz, CDCl$_3$) δ 6.01 (m, 1H), 4.97 (s, 1H), 4.69 (m, 1H), 3.96-3.87 (m, 4H), 2.47-2.43 (m, 1H), 2.17-1.10 (m, 21H), 0.90 (s, 3H).

EXAMPLE 54

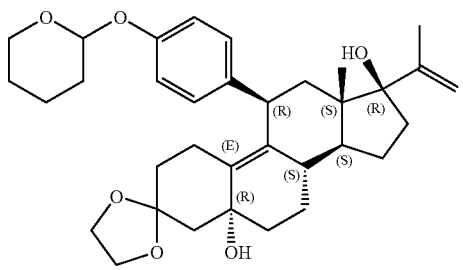

The title compound was prepared according to the procedure in Example 9 above, starting from the compound prepared as in Example 53 above, (1.0 g, 2.68 mmol). The title compound was obtained as white solid.

MH(−water)=533.3.

EXAMPLE 55

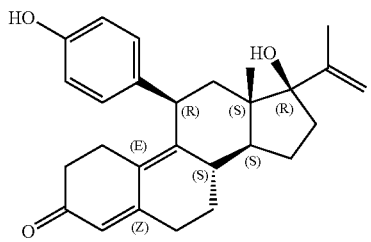

The title compound was prepared according to the procedure in Example 10 above, starting from the compound prepared as in Example 54 above (148 mg, 2.68 mmol). The title compound was obtained as white solid, as a mixture of rotamers.

MH+=405.3 $^1$H NMR (400 MHz, CDCl$_3$) δ 7.01 (d, J=8.4 Hz, 2H), 6.74 (d, J=8.7 Hz, 2H), 5.75 (s, 0.4H), 5.65 (m, 0.6H), 5.12 (s, 0.4H), 5.09 (s, 0.6H), 4.96 (s, 1H), 4.97 (s, 1H), 4.27 (d, 0.4H), 4.20 (s, 0.6H), 2.72-1.25 (m, 20H), 0.87 (s, 1.8H), 0.62 (s, 1.2H).

EXAMPLE 56

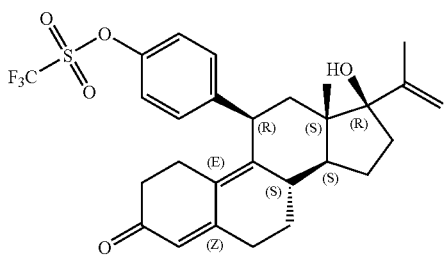

The title compound was prepared according to the procedure in Example 11 above, starting from the compound prepared as in Example 54 above, (380 mg, 0.94 mmol). The title compound was obtained as white solid.

MH+=537.2, M+Na=559.2 $^1$H NMR (400 MHz, CDCl$_3$) δ 7.28-7.26 (m, 2H), 7.20-7.18 (m, 2H), 5.78 (s, 1H), 5.10 (s, 1H), 4.73 (s, 1H), 4.36 (d, J=7.3 Hz, 1H), 3.98-3.90 (m, 1H), 2.75-1.43 (m, 19H), 0.57 (s, 3H).

EXAMPLE 57

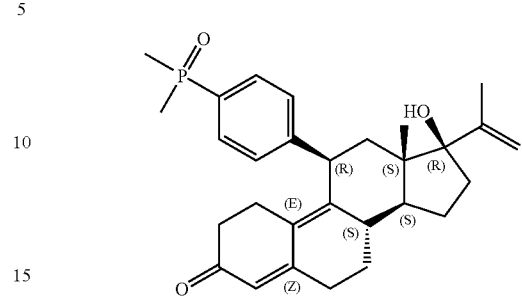

The title compound was prepared according to the procedure in Example 12 above, starting from the compound prepared as in Example 33 above, (50 mg, 0.093 mmol). The title compound was obtained as white solid.

MH+=465.3, M+Na=487.2. $^1$H NMR (400 MHz, CDCl$_3$) δ 7.64 (dd, J=8.1 and 11.3 Hz, 2H), 7.33-7.25 (m, 2H), 5.78 (s, 1H), 5.10 (s, 1H), 4.73 (s, 1H), 4.37 (d, J=7.3 Hz, 1H), 2.70-1.24 (m, 26H), 0.57 (s, 3H).

EXAMPLE 58

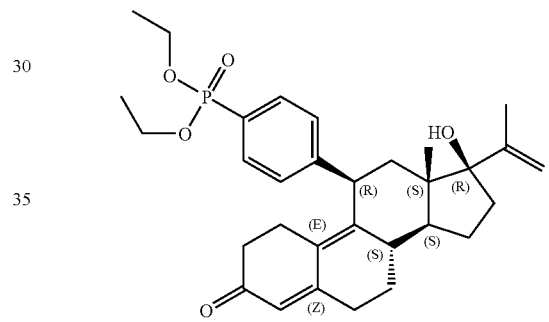

The title compound was prepared according to the procedure in Example 12 above, starting from the compound prepared as in Example 33 above (100 mg, 0.186 mmol). The title compound was obtained as white solid.

MH+=525.3, M+Na=547.2 $^1$H NMR (400 MHz, CDCl$_3$) δ 7.72 (dd, J=8.2 and 13.0 Hz, 2H), 7.30-7.27 (m, 2H), 5.78 (s, 1H), 5.09 (s, 1H), 4.73 (s, 1H), 4.37 (d, J=6.9 Hz, 1H), 4.17-4.05 (m, 4H), 2.70-11.25 (m, 26H), 0.56 (s, 3H).

EXAMPLE 59

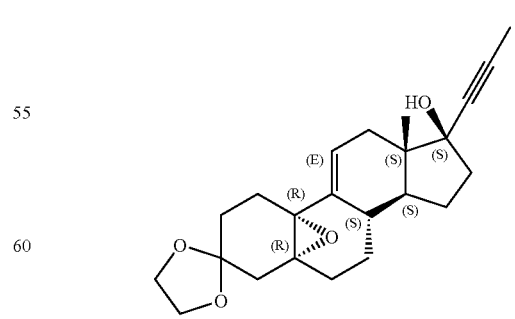

The title compound was prepared according to the procedure in Example 7 above, starting from the compound prepared as in Example 4 above (8.05 g, 22.7 mmol). The title compound was obtained as white solid.

MH+=371.2. ¹H NMR (400 MHz, CDCl₃) δ 6.08 (m, 1H), 3.96-3.87 (m, 4H), 2.65-2.60 (m, 1H), 2.52-2.47 (m, 1H), 2.23-1.20 (m, 20H), 0.82 (s, 3H).

EXAMPLE 60

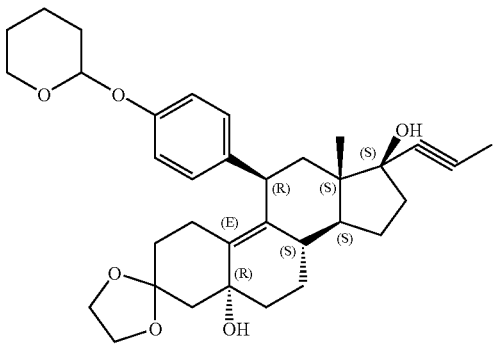

The title compound was prepared according to the procedure in Example 9 above, starting from the compound prepared as in Example 11 (3,3-Ethylenedioxy-5α-hydroxy-11β-[4-(2-tetrahydro-2-H-pyranoxy)-phenyl)-estr-9-en-17-one) (2.7 g, 7.29 mmol). The title compound was obtained as white solid.

M+Na=571.2. MH(–water)=531.2 ¹H NMR (400 MHz, CDCl₃) δ 7.10 (d, J=8.6 Hz, 2H), 6.92 (d, J=8.3 Hz, 2H), 5.35-5.30 (m, 1H), 4.43-4.42 (m, 1H), 4.28 (narrow d, 1H), 4.02-3.91 (m, 4H), 3.64-3.58 (m, 1H), 2.49-1.26 (m, 29H), 0.46 (s, 3H).

EXAMPLE 61

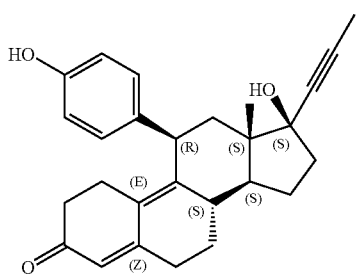

The title compound was prepared according to the procedure in Example 10 above, starting from the compound prepared as in Example 60 above (290 mg, 5.29 mmol). The title compound was obtained as a residue in used in subsequent steps without further purification.

MH+=403.1 ¹H NMR (400 MHz, CDCl₃) δ 7.00 (d, J=8.5 Hz, 2H), 6.74 (d, J=8.5 Hz, 2H), 5.79 (s, 1H), 4.35 d, J=7.1 Hz, 1H), 3.95-3.85 (m, 2H), 2.60-1.30 (m, 19H), 0.52 (s, 3H).

EXAMPLE 62

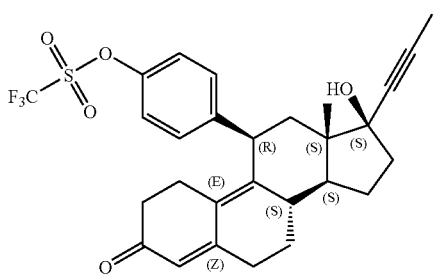

The title compound was prepared according to the procedure in Example 11 above, starting from the compound prepared as in Example 61 above (2.1 g, 5.29 mmol). The title compound was obtained as white solid.

MH+=535.0, M+Na=557.1 ¹H NMR (400 MHz, CDCl₃) δ 7.27 (d, J=8.3 Hz, 2H), 7.20 (d, J=8.9 Hz, 2H), 5.80 (s, 1H), 4.45 (d, J=7.3 Hz, 1H), 2.79-2.73 (m, 1H), 2.61-2.58 (m, 2H), 2.47-1.30 (m, 17H), 0.47 (s, 3H).

EXAMPLE 63

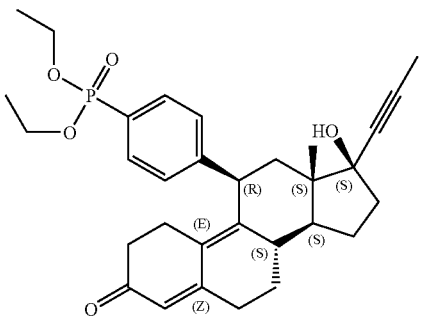

The title compound was prepared according to the procedure in Example 12 above, starting from the compound prepared as in Example 62 above (200 mg, 0.374 mmol). The title compound was obtained as white solid.

MH+=523.5, M+Na=545.5 ¹H NMR (400 MHz, CDCl₃) δ 7.74-7.69 (m, 2H), 7.31-7.28 (m, 2H), 5.79 (s, 1H), 4.46 (d, J=7.4 Hz, 1H), 4.17-4.05 (m, 4H), 2.77-2.70 (m, 1H), 2.60-2.55 (m, 2H), 2.50-1.40 (m, 23H), 0.47 (s, 3H).

EXAMPLE 64

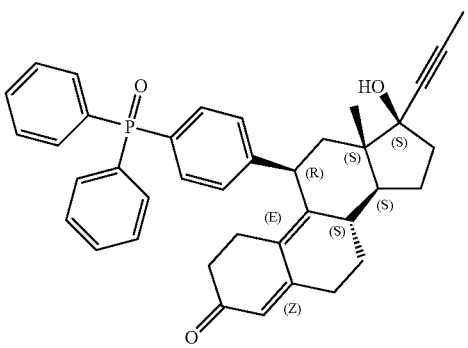

The title compound was prepared according to the procedure in Example 12 above, starting from the compound prepared as in Example 62 above (200 mg, 0.374 mmol). The title compound was obtained as white solid.

MH+=586.8. ¹H NMR (400 MHz, CDCl₃) δ 7.67-7.62 (m, 4H), 7.57-7.53 (m, 4H), 7.48-7.43 (m, 4H), 7.31-7.28 (m, 2H), 5.77 (s, 1H), 4.47 (d, J=7.2 Hz, 1H), 2.80-2.70 (m, 1H), 2.58-2.52 (m, 2H), 2.48-1.30 (m, 17H), 0.49 (s, 3H)

EXAMPLE 65

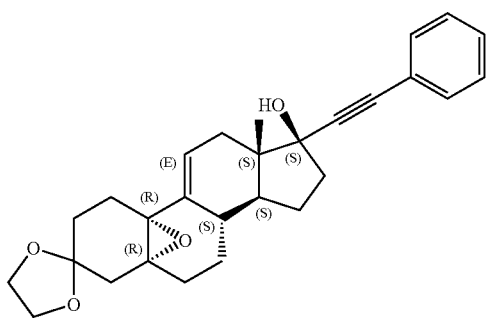

The title compound was prepared according to the procedure in Example 7, starting from the compound prepared as in Example 5 above (2.66 g, 6.39 mmol). The title compound was obtained as white solid.

M+Na=455.2 $^1$H NMR (400 MHz, CDCl$_3$) δ 7.44-7.38 (m, 3H), 7.32-7.28 (m, 2H), 6.10 (t, J=2.6 Hz, 1H), 3.96-3.88 (m, 4H), 3.79-3.70 (m, 1H), 3.00-1.15 (m, 19H), 0.90 (d, J=3.3 Hz, 3H).

EXAMPLE 66

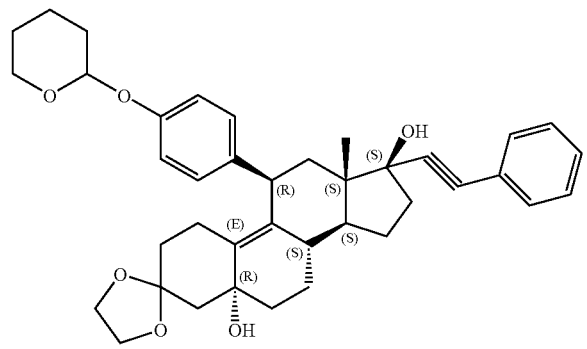

Procedure A:

The title compound was prepared according to the procedure in Example 9 above, starting from the compound prepared as in Example 41 (1.0 g, 2.31 mmol). The title compound was obtained as a white solid.

Procedure B:

The title compound was prepared according to the procedure as described in Example 30, procedure B (3,3-Ethylenedioxy-5a-hydroxy-11b-[4-(2-tetrahydro-2-H-pyranoxy)-phenyl]-estr-9-en-17-one) (2.97 g, 5.84 mmol) and phenyl acetylene magnesium bromide, above. The title compound was obtained as a white solid.

M+Na=633.3, MH(−water)=593.3 $^1$H NMR (400 MHz, CDCl$_3$) δ 7.47-7.44 (m, 2H), 7.35-7.28 (m, 3H), 7.12 (d, J=8.3 Hz, 2H), 6.93 (d, J=7.7 Hz, 2H), 5.37-5.33 (m, 1H), 4.34 (d, J=3.9 Hz, 1H), 4.30 (d, J=6.8 Hz, 1H), 4.04-3.88 (m, 4H), 3.62-3.59 (m, 1H), 2.45-1.30 (m, 26H), 0.53 (d, J=1.5 Hz, 3H).

EXAMPLE 67

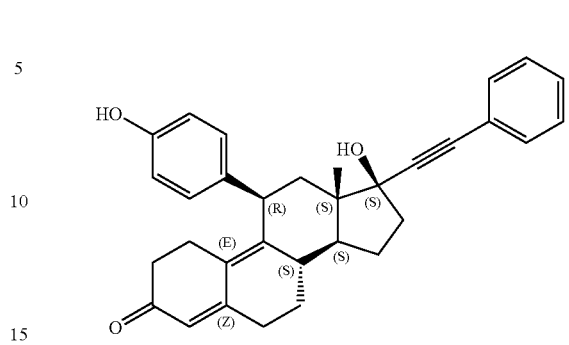

The title compound was prepared according to the procedure in Example 10 above, starting from the compound prepared as in Example 66 above (213 mg, 0.35 mmol). The title compound was obtained as white solid.

MH+=464.9 $^1$H NMR (400 MHz, CDCl$_3$) δ 7.47-7.45 (m, 2H), 7.34-7.32 (m, 3H), 7.04 (d, J=8.4 Hz, 2H), 6.75 (d, J=8.6 Hz, 2H), 5.78 (s, 1H), 4.38 (d, J=7.0 Hz, 1H), 2.78-2.70 (m, 1H), 2.60-2.55 (m, 2H), 2.49-1.45 (m, 15H), 0.59 (s, 3H).

EXAMPLE 68

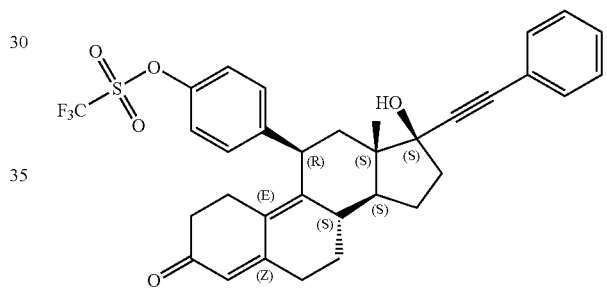

The title compound was prepared according to the procedure in Example 11 above, starting from the compound prepared as in Example 67 above (161 mg, 0.347 mmol). The title compound was obtained as white solid.

MH+=597.2, M+Na=619.0 $^1$H NMR (400 MHz, CDCl$_3$) δ 7.48-7.44 (m, 2H), 7.38-7.20 (m, 7H), 5.80 (s, 1H), 4.47 (d, J=6.9 Hz, 1H), 2.78-2.72 (m, 1H), 2.60-1.40 (m, 16H), 0.54 (s, 3H).

EXAMPLE 69

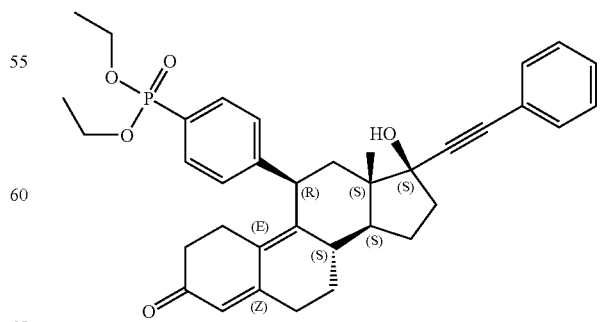

The title compound was prepared according to the procedure in Example 12 above, starting from the compound prepared as in Example 68 above (50 mg, 0.084 mmol). The title compound was obtained as white solid.

MH+=585.2, M+Na=607.2 $^1$H NMR (400 MHz, CDCl$_3$) δ 7.76-7.70 (m, 2H), 7.47-7.45 (m, 2H), 7.35-7.30 (m, 5H), 5.79 (s, 1H), 4.50 (d, J=6.2 Hz, 1H), 4.15-4.08 (m, 4H), 2.76-2.70 (m, 1H), 2.61-2.25 (m, 9H), 2.10-2.04 (m, 4H), 1.85-1.76 (m, 2H), 1.56-1.40 (m, 1H), 1.32 (t, J=7.0 Hz, 6H), 0.54 (s, 3H).

EXAMPLE 70

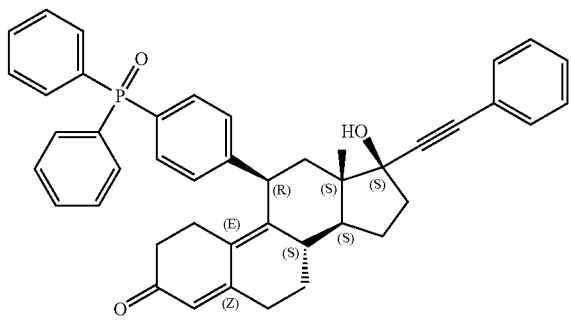

The title compound was prepared according to the procedure in Example 12 above, starting from the compound prepared as in Example 68 above (50 mg, 0.084 mmol). The title compound was obtained as white solid.

MH+=649, M+Na=671.1, MH-=647.1 $^1$H NMR (400 MHz, CDCl$_3$) δ 7.67-7.63 (m, 4H), 7.59-7.53 (m, 4H), 7.48-7.44 (m, 6H), 7.34-7.30 (m, 5H), 5.77 (s, 1H), 4.49 (d, J=7.0 Hz, 1H), 2.78-2.72 (m, 1H), 2.59-2.24 (m, 9H), 2.09-2.02 (m, 3H), 1.85-1.77 (m, 2H), 1.51-1.40 (m, 2H), 0.56 (s, 3H).

EXAMPLE 71

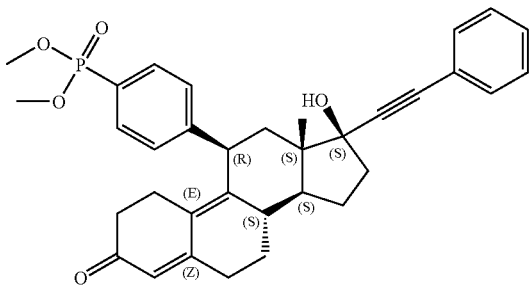

The title compound was prepared according to the procedure in Example 12 above, starting from the compound prepared as in Example 68 above (50 mg, 0.084 mmol). The title compound was obtained as white solid.

M+Na=579, MH-=555.2 $^1$H NMR (400 MHz, CDCl$_3$) δ 7.75-7.70 (m, 2H), 7.48-7.45 (m, 2H), 7.35-7.31 (m, 5H), 5.79 (s, 1H), 4.49 (d, J=7.3 Hz, 1H), 3.98-3.78 (s, 3H), 3.75 (s, 3H), 2.77-1.22 (m, 17H), 0.54 (s, 3H).

One skilled in the art will recognize that, in addition to following the procedures as described in the Schemes detailed above, additional compounds of formula (I) may be similarly prepared according to the procedures as described in Examples 1-71 above.

EXAMPLE 72

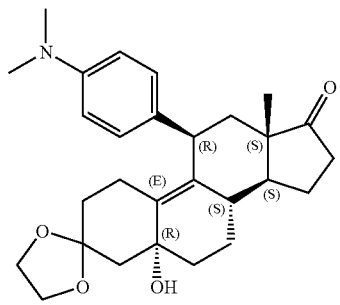

Copper chloride (1.24 g, 12.51 mmol, 1.3 equivalents) was placed in a round-bottom, flask under nitrogen and to the mixture was then added 4-(N,N-dimethyl)anilinemagnesium bromide (50 mL, 0.5M in THF, 25 mmol, 2.6 equivalents). The reaction mixture was stirred vigorously for 5 minutes until all of the copper chloride dissolved. To the reaction mixture was then added a solution of the 3,3-ethylenedioxy-5a-10a-epoxyestr-9,11-en-17-one (3.2 g, 9.62 mmol) in THF (50 mL). The reaction mixture became white and cloudy, was stirred for 1 hour at room temperature and then saturated ammonium chloride solution was added. The aqueous solution was extracted twice with ethyl acetate, dried over magnesium sulfate, filtered and the solvent evaporated. The residue was purified by column chromatography eluting with 10 to 100% ethyl acetate/hexanes to yield the title compound as an off-white solid.

1H NMR (CDCl$_3$) δ 7.02 (d, 2H, J=9.2 Hz), 6.62 (d, 2H, J=9.2 Hz), 4.38-3.85 (m, 5H), 2.92 (s, 6H), 2.48-1.56 (m, 19H), 0.51 (s, 3H).

MS: MH+ (478)

EXAMPLE 73

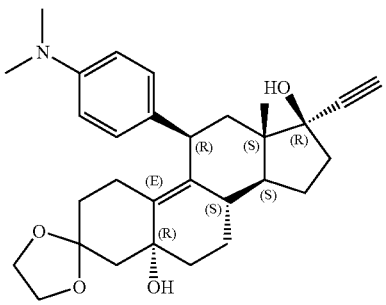

To a solution of the 3,3-ethylenedioxy-5a-hydroxy-11b-[4-(N,N-dimethylamino)phenyl]-estr-9-en-17-one (1.1 g, 2.44 mmol) in THF (20 mL) was added ethynyl MgBr (0.5 M in THF, 11.76 mL, 5.88 mmol). After 16 hours at room temperature, the reaction mixture was partitioned between EtOAc/aqueous NH$_4$Cl solution. The organic layer was separated, dried and concentrated. The crude product was purified on silica gel column (3:7 EtOAc/Hex.) to yield the title compound as a white solid.

1H NMR (CDCl$_3$) δ 7.08 (d, 2H, J=9.1 Hz), 6.68 (d, 2H, J=9.1 Hz), 4.42-3.85 (m, 5H), 2.91 (s, 6H), 2.42-1.56 (m, 19H), 0.52 (s, 3H).

MS: MH+ (478)

EXAMPLE 74

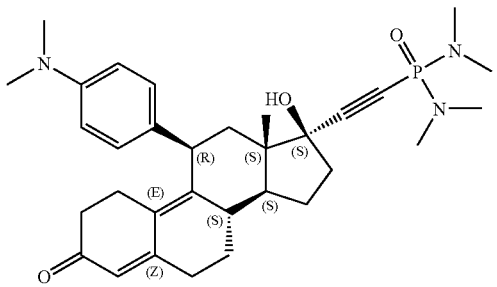

To a solution of the 3,3-ethylenedioxy-5a,17b-dihydroxy-11b-[4-(N,N-dimethylamino)phenyl]-19-nor-17a-pregn-9-ene-21-ethyne (50 mg, 0.1048 mmol) in THF (5 mL), as added LHMDS (0.35 mL, 1.0 M) at room temperature. After 30 min, bis(dimethylamino)phosphoryl chloride (59 mg, 0.3459 mmol) was added. The reaction mixture was stirred at room temperature for 16 h. To the reaction mixture was then added p-TSA.H$_2$O (10 mg). After stirring at 50° C. for 1 hour, the crude reaction mixture was partitioned between EtOAc/aqueous NaHCO$_3$ solution. The organic layer was isolated, dried and concentrated. The resulting crude residue was purified on prep. TLC to yield the title compound as a white solid.

$^1$H NMR (CDCl$_3$) δ 7.08 (m, 2H), 6.62 (m, 2H), 5.72 (s, 1H), 4.38~3.62 and 2.98~1.29 (m, 36H), 0.55 (s, 3H).

MS (m/e): 550 (MH$^+$).

EXAMPLE 75

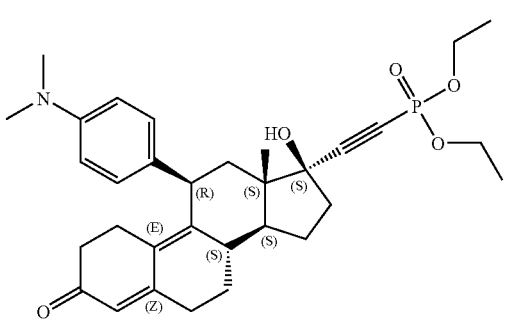

The title compound was prepared according to the procedure in Example 74 above, starting from the compound prepared as in Example 73 above, (82 mg, 0.133 mmol). The title compound was obtained as white solid.

$^1$H NMR (CDCl$_3$) δ 7.02 (d, 2H, J=9.4 Hz), 6.62 (d, 2H, J=9.4 Hz), 5.78 (s, 1H), 4.38 (m, 1H), 4.10 (m, 4H), 2.94~1.26 (m, 29H), 0.61 (s, 3H).

MS (m/e): 552 (MH$^+$)

EXAMPLE 76

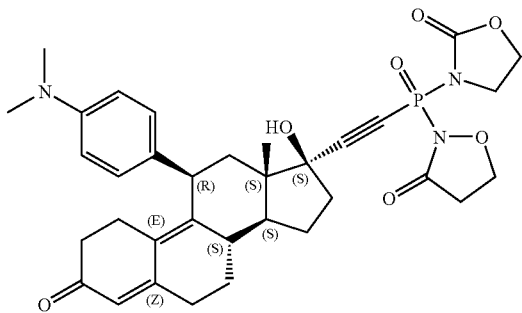

The title compound was prepared according to the procedure in Example 74 above, starting from the compound prepared as in Example 73 above (50 mg, 0.10 mmol). The title compound was obtained as white solid.

$^1$H NMR (CDCl$_3$) δ 7.02 (d, 2H, J=9.4 Hz), 6.62 (d, 2H, J=9.4 Hz), 5.78 (s, 1H), 4.41 (m, 4H), 4.10 (m, 4H), 2.94~1.42 (m, 24H), 0.61 (s, 3H).

MS (m/e): 634 (MH$^+$), 656 (MNa$^+$).

EXAMPLE 77

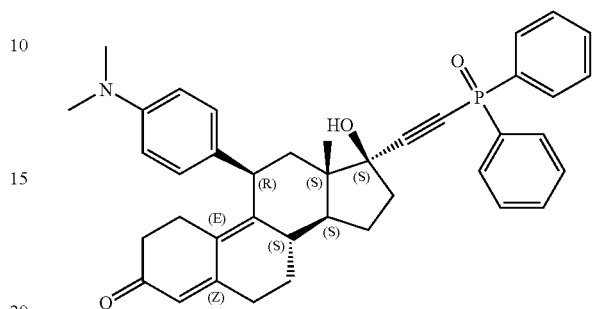

The title compound was prepared according to the procedure in Example 74 above, starting from the compound prepared as in Example 73 above (0.10 g, 0.21 mmol). The title compound was obtained as white solid.

$^1$H NMR (CDCl$_3$) δ 7.78 (m, 5H), 7.48 (m, 5H), 7.02 (d, 2H, J=9.4 Hz), 6.62 (d, 2H, J=9.4 Hz), 5.74 (s, 1H), 4.38 (m, 1H), 2.94~1.26 (m, 23H), 0.72 (s, 3H).

MS (m/e): 616 (MH$^+$).

EXAMPLE 78

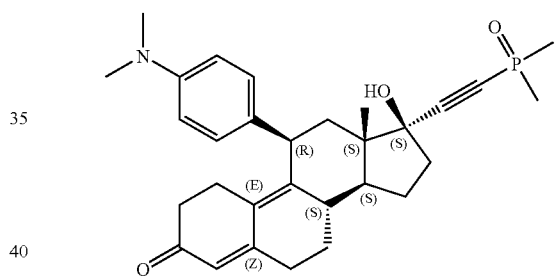

The title compound was prepared according to the procedure in Example 74 above, starting from the compound prepared as in Example 73 above (108 mg, 0.2264 mmol). The title compound was obtained as white solid.

$^1$H NMR (CDCl$_3$) δ 7.02 (d, 2H, J=9.4 Hz), 6.68 (d, 2H, J=9.4 Hz), 5.74 (s, 1H), 4.38 (m, 1H), 2.94~1.26 (m, 29H), 0.61 (s, 3H).

MS (m/e): 492 (MH$^+$), 514 (MNa$^+$).

EXAMPLE 79

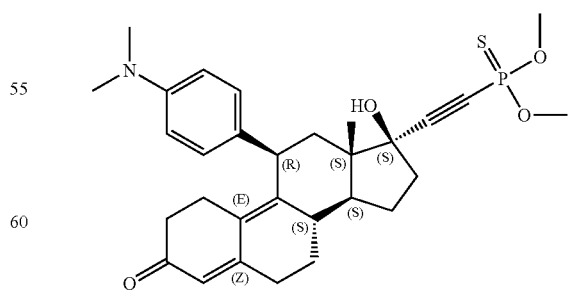

The title compound was prepared according to the procedure in Example 74 above, starting from the compound prepared as in Example 73 above (100 mg, 0.21 mmol). The title compound was obtained as white solid.

¹H NMR (CDCl₃) δ 7.02 (d, 2H, J=9.4 Hz), 6.68 (d, 2H, J=9.4 Hz), 5.74 (s, 1H), 4.38 (m, 1H), 3.75 (m, 6H, 2-OMe), 2.94~1.26 (m, 23H), 0.61 (s, 3H).

MS (m/e): 540 (MH⁺), 562 (MNa⁺).

EXAMPLE 80

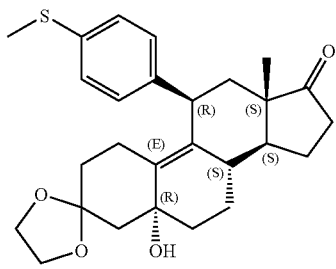

A solution of 4-thioanisolemagnesium bromide (0.5M, 100 mL, 50 mmol) was added to copper (I) chloride (2.49 g, 25.18 mmol) and stirred rapidly. The reaction mixture released heat and turned green and cloudy. When the heat dissipated and most of the solid dissolved, a solution of 3,3-ethylenedioxy-5a,10a-epoxyestr-9,11-en-17-one (6.4 g, 19.37 mmol) in THF (100 mL) was added. The reaction mixture turned brown immediately and became cloudy. After stirring 2 hours, saturated ammonium chloride was added. The reaction mixture was then extracted twice with ethyl acetate and the extracts washed with brine, dried over magnesium sulfate, filtered, and the solvent then evaporated. The resulting off-white solid was taken up in dichloromethane and filtered. This was repeated 4 times. The filtrate was purified by column chromatography eluting with 20 to 95% ethyl acetate/hexanes to yield the title compound as a white solid.

M+Na=477.0, MH(−water)=437.1. ¹H NMR (400 MHz, CDCl₃) δ 7.14 (s, 4H), 4.38 (s, 1H), 4.28 (d, J=6.9 Hz, 1H), 4.04-3.91 (m, 4H), 2.46-2.25 (m, 10H), 2.11-1.21 (m, 11H), 0.50 (s, 3H).

EXAMPLE 81

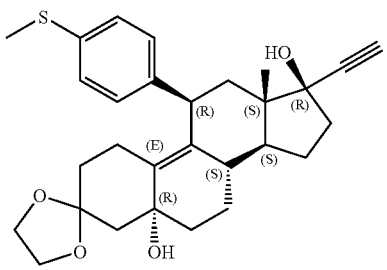

A solution of the compound prepared as in Example 80 above (1.77 g, 3.89 mmol) in THF (35 mL) was prepared. A solution of ethynylmagnesium bromide was added (0.5M, 31 mL, 15.56 mmol) and the resulting mixture was stirred at room temperature for 3 hours under nitrogen. A solution of saturated ammonium chloride was then added. The reaction mixture was extracted twice with ethyl acetate, dried, filtered and the solvent evaporated. The resulting residue was purified by column chromatography (10 to 60% ethyl acetate/hexanes) to yield the title compound as white solid.

M+Na=503.2, MH(−water)=463.2. ¹H NMR (400 MHz, CDCl₃) δ 7.14 (s, 4H), 4.39 (s, 1H), 4.29 (d, J=7.4 Hz, 1H), 4.04-3.88 (m, 4H), 2.60 (s, 1H), 2.47-1.49 (m, 22H), 0.47 (s, 3H).

EXAMPLE 82

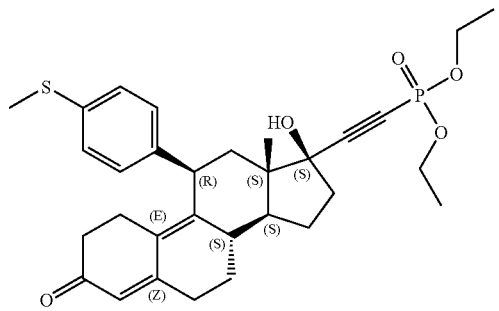

A solution of the compound prepared as in Example 81 above (50 mg, 0.104 mmol) in THF (8 mL) was prepared in 50 mL round bottom flask. A solution of lithium hexamethyldisilazide in toluene (1.0M, 0.34 mL, 0.343 mmol) was added and the resulting mixture was stirred for 30 minutes. A solution of diethyl chlorophosphate (0.05 mL, 0.343 mmol) in THF (1 mL) was then added and the reaction mixture was stirred overnight at room temperature under nitrogen. The reaction mixture was quenched with aqueous saturated ammonium chloride and extracted mixture twice with ethyl acetate. The organic extracts were dried over magnesium sulfate, filtered, and the solvent evaporated to yield crude product. The crude product was used for next step without purification.

A solution of the crude product prepare above (64 mg, 0.104 mmol) in acetone (3 mL) was prepared. Oxalic acid (29 mg, 0.230 mmol) in a minimal amount of water was added and the resulting mixture was heated to 60° C. for 2 hours. Water was then added to the reaction mixture. The aqueous layer was extracted twice with ethyl acetate. The combined organic layers washed with brine, dried, filtered and the solvent evaporated to yield a yellow residue. The residue was purified by prep TLC eluting with 80% ethyl acetate/hexanes to yield the title compound MH+=555.2, M+Na=577.2. ¹H NMR (400 MHz, CDCl₃) δ 7.49 (d, J=8.3 Hz, 1H), 7.32 (d, J=8.4 Hz, 1H), 7.18 (d, J=8.7 Hz, 1H), 7.10 (d, J=8.3 Hz, 1H), 5.78 (s, 1H), 4.40-4.36 (m, 1H), 4.16-4.04 (m, 4H), 2.80-1.25 (m, 26H), 0.58 (s, 3H).

EXAMPLE 83

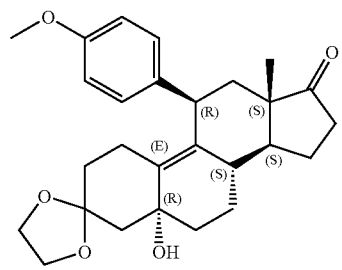

The title compound was prepared according to the procedure in Example 72 above, starting from the compound prepared as in Example 7 above (2.85 g, 8.66 mmol). The title compound was obtained as white solid.

$^1$H NMR (CDCl$_3$) δ 7.14 (d, 2H, J=9.1 Hz), 6.81 (d, 2H, J=9.1 Hz), 4.3 (m, 1H), 4) (m, 4H), 3.78 (s, 3H), 2.42-1.56 (m, 18H), 0.5 (s, 3H).

MS: (M−18)+ (421), MNa+ (461)

EXAMPLE 84

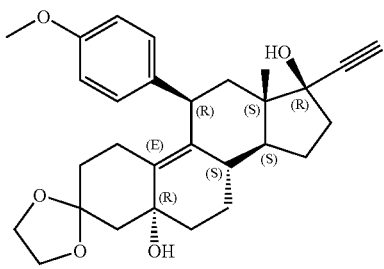

The title compound was prepared according to the procedure in Example 73 above, starting from the compound prepared as in Example 83 above (1.26 g, 2.88 mmol). The title compound was obtained as white solid.

EXAMPLE 85

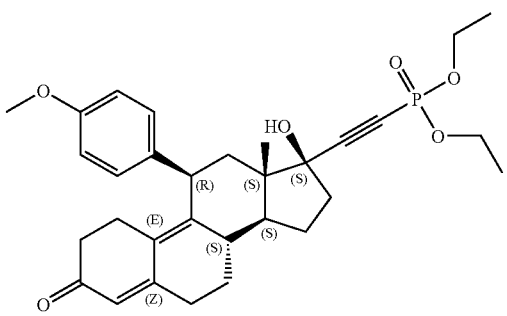

The title compound was prepared according to the procedure in Example 74 above, starting from the compound prepared as in Example 84 above (85 mg, 0.183 mmol). The title compound was obtained as white solid.

$^1$H NMR (CDCl$_3$) δ 7.09 (d, 2H, J=9.4 Hz), 6.81 (d, 2H, J=9.4 Hz), 5.78 (s, 1H), 4.38 (m, 1H), 4.28~4.08 (m, 7H), 2.82~1.26 (m, 23H), 0.61 (s, 3H).

MS (m/e): 539 (MH$^+$).

EXAMPLE 86

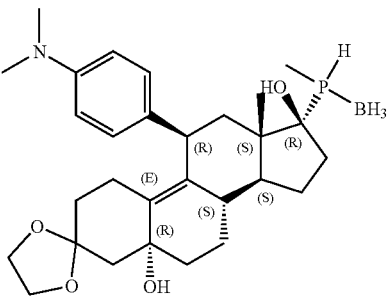

At −78° C. in a 50 mL round bottom flask was placed THF (2.5 mL) and CH$_3$PH$_2$.BH$_3$ (0.047 g, 0.75 mmol). n-BuLi (0.3 mL, 2.5 M in hexanes, 0.75 mmol) was added and the resulting mixture was stirred at −78° C. for 1 h. The compound prepared as in Example 72 above (0.113 g, 0.25 mmol) in THF (2.5 mL) was then added. The reaction mixture was slowly warmed up to room temperature. The reaction mixture was quenched with water. The reaction mixture was extracted with EtOAc (2×50 mL), then dried and concentrated, to yield crude product which was purified by prep. TLC (3:7 EtOAc/Hex) to yield the title compound as a residue.

MH+ (514) 1H NMR (CDCl$_3$) δ 7.08 (m, 2H), 6.68 (m, 2H), 4.32 (m, 1H), 3.92 (m, 4H), 3.50 (d, 1H, J=3.1 Hz), 2.41-1.3 (m, 29H), 1.21 (s, 3H), 0.52 (d, 3H, J=4.1 Hz).

EXAMPLE 87

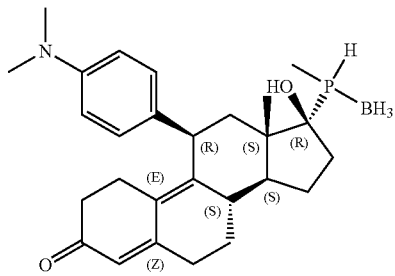

The compound prepared as in Example 86 above 11 (50 mg, 0.097 mmol) was stirred with p-TSA.H$_2$O (5 mg) in acetone (10 mL) at 60° C. for 1.5 h. The resulting mixture was then partitioned in 50 mL EtOAc/50 mL water. The organic layer was dried and concentrated to yield a brown oil. The brown oil was purified on prep. TLC (10% EtOAc/Hexane) to yield the title compound as an off-white solid.

MH+ (452), 2MNa+ (925) $^1$H NMR (CDCl$_3$) δ 7.08 (d, 2H, J=9.2 Hz), 6.66 (d, 2H, J=9.2 Hz), 5.72 (s, 1H), 5.5 (m, 1H), 4.30 (m, 2H), 3.5 (s, 1H), 2.91-1.22 (m, 27H). 0.52 (d, 3H, J=6.1 Hz).

EXAMPLE 88

19,24-Dinorchola-4,9,20-trien-3-one, 17,23-epoxy-1-(4-(hydroxy-methoxy-phosphorylphenyl)-, (11β, 17α)-(9Cl) (Compound #17)

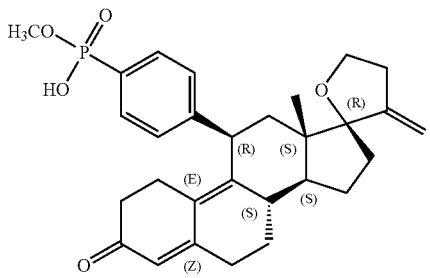

A mixture of 19,24-dinorchola-4,9,20-trien-3-one, 17,23-epoxy-11-(4-(dimethoxy-phosphorylphenyl)-, (11β,17α)-(9Cl) prepared as in Example 27, above (80 mg, 0.157 mmol) in tBuOH (2.4 mL), water (1.2 mL) and LiOH (8 mg, 0.314 mmol) was stirred at 80° C. for 2.5 hours. The resulted solution was partitioned between EtOAc/water (50 mL/50 mL). The organic layer was dried and concentrated. The resulted crude material was purified by preparative TLC (30% MeOH/dichloromethane) to yield the title compound as a residue.

¹H NMR δ (MeOD) δ 7.70 (m, 2H), 7.21 (m, 2H), 5.70 (s, 1H), 5.18 (s, 1H), 4.42 (d, 1H, J=5.8 Hz), 3.80 (m, 3H), 3.42 (m, 4H), 2.78~1.08 (m, 17H), 0.58 (s, 3H).
MS: MH+ (495), MNa+ (517). 2 MH+ (989), 2MNa+ (1011).

EXAMPLE 89

19,24-Dinorchola-4,9,20-trien-3-one, 1723-epoxy-11-[4-(hydroxy-methyl-phosphinoyl)phenyl]-(11β,17α)-(9Cl) (Compound #22)

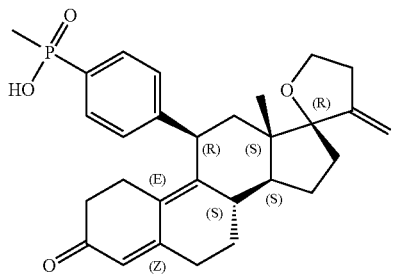

19,24-Dinorchola-4,9,20-trien-3-one, 17,23-epoxy-1-[4-(ethoxy-methyl-phosphinoyl)phenyl]-, (11β,17α)-(9Cl), the compound prepared as in Example 28 (14.8 mg, 0.0327 mmol) and LiOH (3.3 mg, 0.137 mmol) was mixed with tBuOH (0.3 g) and water (50 μL). After stirring the reaction mixture at 90° C. for 30 min, the reaction mixture was partitioned between EtOAc/water (50 mL/50 mL). The organic layer washed with NaHCO₃ (aq.) and then brine. The resulting solution was dried and concentrated, and the resulting crude oil was purified by preparative TLC (30% MeOH/dichloromethane) to yield the title compound as a residue.

¹H NMR (MeOD) δ 7.68 (m, 2H), 7.21 (m, 2H), 5.72 (s, 1H), 5.68 (s, 1H), 4.42 (d, 1H), 3.80 (m, 2H), 2.78~1.29 (m, 22H), 0.56 (s, 3H). $C_{29}H_{35}O_4P$
MS: MNa⁺ (501), MH⁻ (477).

EXAMPLE 90

19,24-Dinorchola-4,9,20-trien-3-one, 17,23-epoxy-11-[4-[Bis-(2,2,2-trifluoro-ethoxy)-phosphoryl]-phenyl]-, (11β,17α)-(9Cl) (Compound #38)

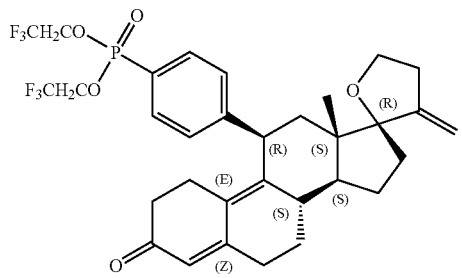

The title compound was prepared as a white solid according to the procedure in Example 12 above, starting from the compound prepared as in Example 24, above.

1H NMR (CDCl3) δ 7.72 (m, 2H), 7.32 (m, 2H), 5.75 (s, 1H), 5.13 (s, 1H), 4.83 (s, 1H), 4.45 (m, 5H), 3.81 (m, 2H), 2.71~1.34 (m, 18H), 0.52 (s, 3H). C32H35F6O5P
MH+=645, M+Na=667.

EXAMPLE 91

19,24-Dinorchola-4,9,20-trien-3-one, 17,23-epoxy-11-[4-(diphenyl-phosphinoyl)-phenyl]-, (11β,17α)-(9Cl) (Compound #36)

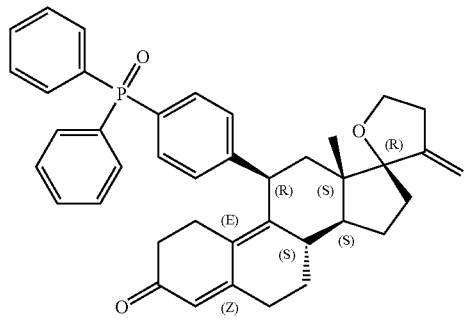

The title compound was prepared as a white solid according to the procedure in Example 12 above, starting from the compound prepared as in Example 24, above.

1H NMR (CDCl₃) δ 8.02 (m, 2H), 7.62~7.42 (m, 12H), 5.72 (s, 1H), 5.12 (s, 1H), 4.82 (s, 1H), 4.33 (d, 1H, =5.9 Hz), 3.81 (m, 2H), 2.71~1.42 (m, 18H), 0.52 (s, 3H). MH+=601, M+Na=623.

EXAMPLE 92

19,24-Dinorchola-4,9,20-trien-3-one, 17,23-epoxy-11-[4-[Bis-(4-chloro-phenyl)-phosphinoyl]-phenyl]-, (11β,17α)-(9Cl) (Compound #39)

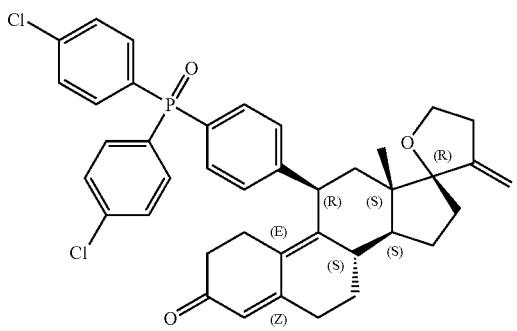

The title compound was prepared as a white solid according to the procedure in Example 12 above, starting from the compound prepared as in Example 24, above.

1H NMR (CDCl₃) δ 7.62~7.28 (m, 12H), 5.72 (s, 1H), 5.13 (s, 1H), 4.83 (s, 1H), 4.32 (d, 1H, J=6.2 Hz), 3.53 (m, 2H), 2.68~1.38 (m, 18H), 0.52 (s, 3H).

MH+=669, M+Na=691.

EXAMPLE 93

19,24-Dinorchola-4,9,20-trien-3-one, 17,23-epoxy-11-(4-(diphenoxy-phosphorylphenyl)-, (11β,17α)-(9Cl) (Compound #37)

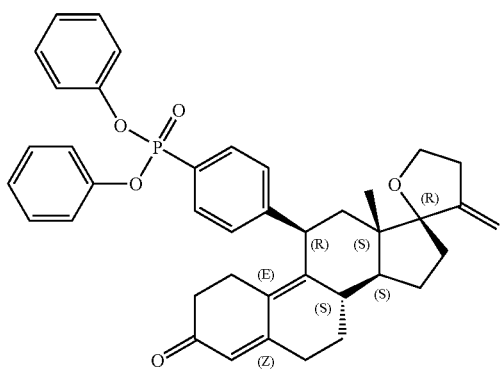

The title compound was prepared as a white solid according to the procedure in Example 12 above, starting from the compound prepared as in Example 24, above.

1H NMR (CDCl$_3$) δ 7.82 (m, 2H), 7.28~7.08 (m, 12H), 5.72 (s, 1H), 5.14 (s, 1H), 4.82 (s, 1H), 4.32 (d, 1H, J=5.8 Hz), 3.82 (m, 2H), 2.71~1.41 (m, 18H), 0.51 (s, 3H).

MH+=633, M+Na=655.

EXAMPLE 94

19,24-Dinorchola-4,9,20-trien-3-one, 17,23-epoxy-11-[4-(5,5-Dimethyl-2-oxo-2λ$^5$-[1,3,2]dioxaphosphinan-2-yl)-phenyl]-, (11β,17α)-(9Cl) (Compound #23)

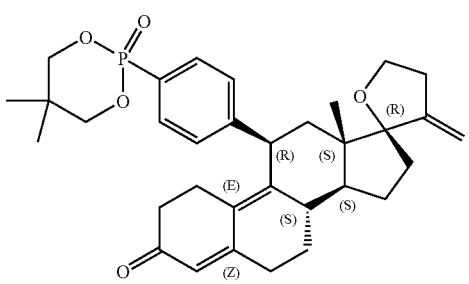

The title compound was prepared as a white solid according to the procedure in Example 12 above, starting from the compound prepared as in Example 24, above.

$^1$H NMR (CDCl3) δ 7.78 (m, 2H), 7.28 (m, 2H), 5.78 (s, 1H), 5.12 (s, 1H), 4.82 (s, 1H), 4.32 (m, 3H), 3.85 (m, 5H), 2.72~1.35 (m, 17H), 1.18 (s, 3H), 1.02 (s, 3H), 0.55 (s, 3H).

MH+=549.3, M+Na=571.3.

One skilled in the art will recognize that, in addition to following the procedures as described in the Schemes detailed above, additional compounds of formula (II) may be similarly prepared according to the procedures as described in Examples 72-94 above.

EXAMPLE 95-97

Example 95

Alkaline Phosphatase Assay in Human Breast Cancer Cell Line T47D

T47D human breast cancer cells were grown in RPMI medium without phenol red (Invitrogen) containing 10% (v/v) heat-inactivated fetal bovine serum (FBS; Hyclone), 1% (v/v) penicillin-streptomycin (Invitrogen), 1% (w/v) glutamine (Invitrogen), and 10 mg/mL insulin (Sigma). Incubation conditions were 37° C. in a humidified 5% (v/v) carbon dioxide environment.

The cells were plated in 96-well tissue culture plates at 10,000 cells per well in assay medium [RPMI medium without phenol red (Invitrogen) containing 5% (v/v) charcoal-treated FBS (Hyclone) and 1% (v/v) penicillin-streptomycin (Invitrogen)]. Two days later, the medium was decanted and test compound or control were added at a final concentration of 0.1% (v/v) dimethyl sulfoxide in fresh assay medium. Twenty-four hours later, an alkaline phosphatase assay was performed using a SEAP kit (BD Biosciences Clontech, Palo Alto, Calif.). Briefly, the medium was decanted and the cells were fixed for 30 minutes at room temperature with 5% (v/v) formalin (Sigma). The cells were washed once with room temperature Hank's buffered saline solution (Invitrogen). Equal volumes (0.05 mL) of 1× Dilution Buffer, Assay Buffer and 1:20 substrate/enhancer mixture were then added. After 1 hour incubation at room temperature in the dark, the lysate was transferred to a white 96-well plate (Dynex) and luminescence was read using a LuminoSkan Ascent (Thermo Electron, Woburn, Mass.).

Example 96

C3 Assay

The complement C3 assay was performed as follows (Lundeen S G, Zhang Z, Zhu Y, Carver J M, Winneker R C. 2001. Rat uterine complement C3 expression as a model for progesterone receptor modulators: characterization of the new progestin trimegestone. J Steroid Biochem Molec Biol 78:137-143).

Ovariectomized two month-old Sprague Dawley rats were purchased from Harlan (Indianapolis, Ind.). Five to seven days after surgery, the rats were dosed once with test compound or control. About 24 h later, the rats were euthanized by carbon dioxide asphyxiation. Whole uteri were removed, trimmed of fat and frozen on dry ice prior to storage at −80° C. The uteri were homogenized in 1 to 2 mL each of TRIzol (Invitrogen Life Technologies, Carlsbad, Calif.); and the homogenates were processed for RNA preparation according to the manufacturer's directions.

Quantitative PCR was performed using rat complement C3 primers and TaqMan probe from Applied Biosystems (Foster City, Calif.) and an ABI PRISM 7000 Sequence Detection System (Applied Biosystems). The level of 28S ribosomal RNA in each sample was determined for normalization, and a dilution series of one of the estrogen-treated samples was used to generate a standard curve.

Example 97

Transient Transfection and Steady Glo Luciferase Assay

A549 Human lung carcinoma cells were grown in F-12K Nutrient Mixture containing 10% (v/v) fetal bovine serum (FBS; Invitrogen), 2 mM glutamine and 0.15% sodium dicarbonate (Invitrogen)

A549 cells were split 1 to 3 in 175 cm tissue culture flask. The cells were incubated at 37° C. in $CO_2$ incubator until the cells were 95% confluent (typically 24-30 hours).

The following solutions were prepared in sterile tubes: (a) Solution A: 1.5 µg/ml of DNA in 8.5 ml OPTI-MEM I Reduced Serum Medium. (GIBCO cat# 31985) and (b) Solution B: 6 µl/ml of DMRIE-C Reagent into 8.5 µl OPTI-MEM I. The two solutions were combined and mixed gently, then incubated at room temperature for 40 minutes.

The A549 cells prepared above were washed with 100 µl of OPTI-MEM I. The medium was removed and 17 ml of the lipid-DNA complex solution was overlayed onto cells. The cells ere then incubated for 16 h at 37° C. in $CO_2$ incubator. The DNA-containing medium was removed and 30 ml of growth medium was added. (5% Charcoal treated FBS) After 5-6 h, the cells were seeded in a 96 well plate and the cells incubated overnight at 37° C. in $CO_2$ incubator.

To each well was then added 5 µl of test compounds and the cells incubated at 37° C. for 10 min. 5 µL of dexamathasone (CAS [50-02-2]), a glucocorticoid agonist, solution was then added to each well for challenger and the cells incubated at 37° C. in $CO_2$ incubator for 24 h. 100 µl of Luc-assay buffer was then added into each cell well and the cells incubated for 30 min at room temperature. A 150 µL sample from each well was then transferred into a DYNEX Microlitel plate and read on Top-counter.

Representative compounds of the present invention were tested according to the procedures described in Examples 95-97 above, with results as listed in Table 3 below.

TABLE 3

| ID No. | T47D $IC_{50}$ (nM) | A549 $IC_{50}$ (nM) |
|---|---|---|
| 1 | >1,000 | 254.4 |
| 2 | >1,000 | >710 |
| 3 | 12 | 237.7 |
| 4 | 3 | 66.15 |
| 5 | 101.5 | ND |
| 6 | >1000 | >3000 |
| 7 | 8.4 | 623.6 |
| 8 | 170 | 168.26 |
| 9 | 205 | >1000 |
| 10 | 18.3 | >3000 |
| 11 | 51.3 | 66.3 |
| 12 | | >3,000 |
| 13 | 170 | 30.2 |
| 14 | | |
| 15 | 8.8 | >3000 |
| 16 | 8.3 | 230 |
| 17 | >1,000 | >3,000 |
| 18 | >1000 | >3,000 |
| 19 | 4.2 | 271 |
| 20 | >1,000 | >3,000 |
| 21 | | >3000 |
| 22 | >1,000 | >3,000 |
| 23 | 28.7 | 64.3 |
| 24 | 762 | 48.2 |
| 25 | 38.2 | 83.79 |
| 26 | 125 | 41.5 |
| 27 | 381 | 16.58 |
| 28 | 660 | 129 |
| 29 | 160 | 225 |

TABLE 3-continued

| ID No. | T47D $IC_{50}$ (nM) | A549 $IC_{50}$ (nM) |
|---|---|---|
| 30 | 275 | 93.01 |
| 31 | 7.47 | 130.41 |
| 32 | >1000 | 217.25 |
| 33 | >1000 | 217.25 |
| 34 | 890 | 817.53 |
| 35 | 980 | 947.5 |
| 36 | 45 | 163.45 |
| 37 | 3.3 | 34.33 |
| 38 | 29.5 | 140.81 |
| 39 | 20 | 143.11 |
| 101 | 1.3 | >100 |
| 102 | 7.3 | 70.42 |
| 103 | 1.57 | 41.61 |
| 104 | 7.25 | 64.05 |
| 105 | 1.44 | 55.78 |
| 106 | 7.53 | 120.94 |
| 107 | 4.75 | 453.78 |
| 108 | 6.9 | 72.18 |
| Formula (III) | | 69.38 |

EXAMPLE 93

As a specific embodiment of an oral composition, 100 mg of the compound #4 is formulated with sufficient finely divided lactose to provide a total amount of 580 to 590 mg to fill a size O hard gel capsule.

EXAMPLE 94

As a specific embodiment of an oral composition, 100 mg of the compound #101 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:
1. A compound of formula (II)

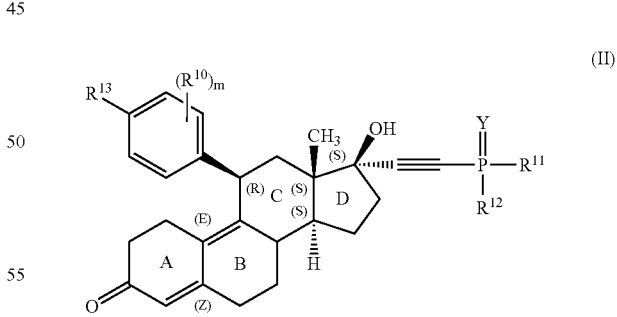

wherein m is an integer from 0 to 3;

$R^{10}$ is selected from the group consisting of hydroxy, halogen, $C_{1-3}$alkyl, $C_{1-3}$alkoxy, cyano, nitro, amino, ($C_{1-4}$alkylamino) and di($C_{1-4}$alkyl)amino;

Y is selected from the group consisting of O and S;

$R^{11}$ and $R^{12}$ are each independently selected from the group consisting of hydroxy, $C_{1-4}$alkyl, —CH(—O—$C_{1-4}$alkyl)$_2$, $C_{1-4}$alkoxy, halogenated $C_{1-4}$alkyl, halogenated $C_{1-4}$alkoxy, phenyl, —O-phenyl, —O-aralkyl, 2-isoxazolidin-3-one and $NR^{15}R^{16}$;

wherein the phenyl, whether alone or as part of a substituent group, is optionally substituted with one or more substituents independently selected from hydroxy, carboxy, halogen, $C_{1-3}$alkyl, $C_{1-3}$alkoxy, cyano, nitro, amino, ($C_{1-4}$alkylamino) and di($C_{1-4}$alkyl)amino;

wherein $R^{15}$ and $R^{16}$ are each independently selected from the group consisting of hydrogen and $C_{1-4}$alkyl; alternatively, $R^{15}$ and $R^{16}$ are taken together with the nitrogen atom to which they are bound to form a 5- to 7-membered saturated or partially unsaturated nitrogen containing heterocyclyl ring; wherein the nitrogen containing heterocyclyl ring is optionally substituted with one or more substituents independently selected from hydroxy, carboxy, $C_{1-4}$alkyl, $C_{1-4}$alkoxy, nitro, cyano, amino, ($C_{1-4}$alkylamino) and di($C_{1-4}$alkyl)amino;

alternatively, $R^{11}$ and $R^{12}$ are taken together with the phosphorous atom to which they are bound to form a 5- to 7-membered saturated phosphorous containing heterocyclyl ring; wherein the phosphorous containing heterocyclyl ring is optionally substituted with one or more substituents independently selected from hydroxy, carboxy, $C_{1-4}$alkyl, $C_{1-4}$alkoxy, nitro, cyano, amino, ($C_{1-4}$alkylamino) and di($C_{1-4}$alkyl)amino;

$R^{13}$ is selected from the group consisting of —$NR^{17}R^{18}$; —O—$R^{19}$ and —S(O)$_{0-2}$—$R^{20}$;

wherein $R^{17}$ and $R^{18}$ are each independently selected from the group consisting of hydrogen and $C_{1-4}$alkyl; alternatively, $R^{17}$ and $R^{18}$ are taken together with the nitrogen atom to which they are bound to form a 5- to 7-membered saturated nitrogen containing heterocyclyl ring; wherein the nitrogen containing heterocyclyl ring is optionally substituted with one or more substituents independently selected from the group consisting of hydroxy, carboxy, $C_{1-4}$alkyl, $C_{1-4}$alkoxy, nitro, cyano, amino, ($C_{1-4}$alkylamino) and di($C_{1-4}$alkyl)amino;

$R^{19}$ is selected from the group consisting of $C_{1-4}$alkyl, —C(O)—$C_{1-4}$alkyl and —C(O)-phenyl;

$R^{20}$ is selected from the group consisting of hydrogen and $C_{1-4}$alkyl;

or a pharmaceutically acceptable salt, ester or prodrug thereof.

2. A compound as in claim 1, wherein m is an integer from 0 to 1;

$R^{10}$ is selected from the group consisting of hydroxy, halogen and $C_{1-3}$alkyl, and $C_{1-3}$alkoxy;

Y is O;

$R^{11}$ and $R^{12}$ are each independently selected from the group consisting of $C_{1-4}$alkyl, $C_{1-4}$alkoxy, fluorinated $C_{1-4}$alkyl, fluorinated $C_{1-4}$alkoxy, phenyl, 2-isoxazolidin-3-one and $NR^{15}R^{16}$; wherein $R^{15}$ and $R^{16}$ are each independently selected from $C_{1-3}$alkyl;

wherein the phenyl, whether alone or as part of a substituent group, is optionally substituted with one to two substituents independently selected from hydroxy, carboxy, halogen, $C_{1-3}$alkyl and $C_{1-3}$alkoxy;

wherein $R^{15}$ and $R^{16}$ are each independently selected from the group consisting of hydrogen and $C_{1-4}$alkyl; alternatively, $R^{15}$ and $R^{16}$ are taken together with the nitrogen atom to which they are bound to form a 5- to 6-membered saturated nitrogen containing heterocyclyl ring; wherein the nitrogen containing heterocyclyl ring is optionally substituted with one to two substituents independently selected from hydroxy, $C_{1-4}$alkyl and $C_{1-4}$alkoxy;

$R^{13}$ is selected from the group consisting of —$NR^{17}R^{18}$, —O—$R^{19}$ and —S—$R^{20}$;

wherein $R^{17}$ and $R^{18}$ are each independently selected from $C_{1-3}$alkyl;

wherein $R^{17}$ and $R^{18}$ are each independently selected from the group consisting of hydrogen and $C_{1-4}$alkyl; alternatively, $R^{17}$ and $R^{11}$ are taken together with the nitrogen atom to which they are bound to form a 5- to 6-saturated membered nitrogen containing heterocyclyl ring; wherein the nitrogen containing heterocyclyl ring is optionally substituted with one to two substituents independently selected from the group consisting of hydroxy, $C_{1-4}$alkyl and $C_{1-4}$alkoxy;

$R^{19}$ is selected from the group consisting of $C_{1-4}$alkyl and —C(O)—$C_{1-3}$alkyl;

$R^{20}$ is selected from the group consisting of hydrogen and $C_{1-4}$alkyl;

or a pharmaceutically acceptable salt, ester or prodrug thereof.

3. A compound as in claim 2, wherein m is 0;

Y is O;

$R^{11}$ is selected from the group consisting of $C_{1-3}$alkyl, $C_{1-3}$alkoxy, phenyl, 2-isoxazolidin-3-one and $NR^{15}R^{16}$; wherein $R^{15}$ and $R^{16}$ are each independently selected from $C_{1-3}$alkyl;

$R^{12}$ is selected from the group consisting of $C_{1-3}$alkyl, $C_{1-3}$alkoxy, phenyl and $NR^{15}R^{16}$; wherein $R^{15}$ and $R^{16}$ are each independently selected from $C_{1-3}$alkyl;

$R^{13}$ is selected from the group consisting of —$NR^{17}R^{17}$, —O—$R^{19}$ and —S—$R^{20}$;

wherein $R^{17}$ and $R^{18}$ are each independently selected from $C_{1-3}$alkyl;

$R^{19}$ is selected from $C_{1-3}$alkyl;

$R^{20}$ is selected from $C_{1-3}$alkyl;

or a pharmaceutically acceptable salt, ester or prodrug thereof.

4. A compound as in claim 3, wherein m is 0;

Y is O;

$R^{11}$ is selected from the group consisting of methyl, methoxy, ethoxy, phenyl, 2-isooxazolidin-3-one and dimethylamino;

$R^{12}$ is selected from the group consisting of methyl, methoxy, ethoxy, phenyl, 2-isooxazolidin-3-one and dimethylamino;

$R^{13}$ is selected from the group consisting of —$N(CH_3)_2$, —O—$CH_3$ and —S—$CH_3$;

or a pharmaceutically acceptable salt, ester or prodrug thereof.

5. A compound as in claim 4, wherein m is 0;

Y is O;

$R^{11}$ is selected from the group consisting of methyl, methoxy, ethoxy and phenyl;

$R^{12}$ is selected from the group consisting of methyl, methoxy, ethoxy and phenyl;

$R^{13}$ is selected from the group consisting of —$N(CH_3)_2$ and —S—$CH_3$;

or a pharmaceutically acceptable salt thereof.

6. A compound as in claim 4, wherein m is 0;

Y is O;

$R^{11}$ is selected from the group consisting of methyl, methoxy, ethoxy, phenyl and 2-isooxazolidin-3-one;

$R^{12}$ is selected from the group consisting of methyl, methoxy, ethoxy, phenyl and 2-isooxazolidin-3-one;

R[13] is selected from the group consisting of —N(CH$_3$)$_2$ and —O—CH$_3$;
or a pharmaceutically acceptable salt thereof.

7. A pharmaceutical composition comprising a pharmaceutically acceptable carrier and a compound of claim 1.

8. A process for making a pharmaceutical composition comprising mixing a compound of claim 1 and a pharmaceutically acceptable carrier.

9. A method of treating a disorder mediated by a progesterone receptor, wherein the disorder is selected from the group consisting of, carcinoma of the breast, and adenocarcinomas of the breast, comprising administering to a subject in need thereof a therapeutically effective amount of the compound of claim 1.

10. A method of treating a disorder mediated by a glucocorticoid receptor wherein the disorder is Type II diabetes mellitus, comprising administering to a subject in need thereof a therapeutically effective amount of the compound of claim 1.

11. A method of treating a disorder mediated by a progesterone receptor, wherein the disorder is selected from the group consisting of carcinoma of the breast and adenocarcinomas of the breast comprising administering to a subject in need thereof a therapeutically effective amount of the composition of claim 7.

12. A method of treating a disorder mediated by a glucocorticoid receptor, wherein the disorder is Type II diabetes mellitus, comprising administering to a subject in need thereof a therapeutically effective amount of the composition of claim 7.

13. The compound formula (III)

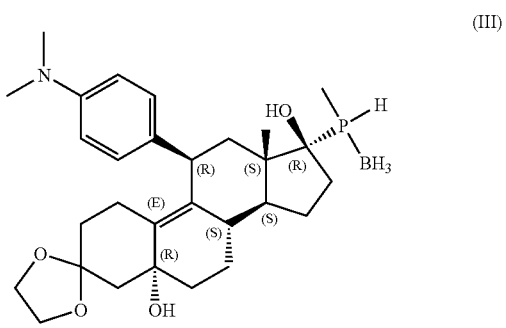

or a pharmaceutically acceptable salt, ester or prodrug thereof.

* * * * *